United States Patent
Kovarik et al.

(10) Patent No.: US 9,072,609 B2
(45) Date of Patent: *Jul. 7, 2015

(54) INTERVERTEBRAL IMPLANT DEVICES FOR SUPPORTING VERTEBRAE AND DEVICES AND METHODS FOR INSERTION THEREOF

(71) Applicant: Pioneer Surgical Technology, Inc., Marquette, MI (US)

(72) Inventors: John Kovarik, Negaunee, MI (US); Allison Rogers, Negaunee, MI (US); Katie S. Barron, Ishpeming, MI (US); Adam MacMillan, Quincy, MA (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/923,463

(22) Filed: Jun. 21, 2013

(65) Prior Publication Data

US 2014/0039624 A1 Feb. 6, 2014

Related U.S. Application Data

(63) Continuation of application No. 12/417,356, filed on Apr. 2, 2009, now Pat. No. 8,470,040.

(60) Provisional application No. 61/041,893, filed on Apr. 2, 2008, provisional application No. 61/042,139, filed on Apr. 3, 2008.

(51) Int. Cl.
*A61F 2/44* (2006.01)
*A61F 2/46* (2006.01)
(Continued)

(52) U.S. Cl.
CPC ............... *A61F 2/447* (2013.01); *A61F 2/4465* (2013.01); *A61F 2002/4475* (2013.01); *A61F 2002/30136* (2013.01); *A61F 2002/30828* (2013.01); *A61F 2/30965* (2013.01); *A61F 2/4611* (2013.01); *A61F 2/4684* (2013.01); *A61F 2002/2817* (2013.01); *A61F 2002/30062* (2013.01); *A61F 2002/30266* (2013.01);
(Continued)

(58) Field of Classification Search
CPC ..................................................... A61F 2/4465
See application file for complete search history.

(56) References Cited

U.S. PATENT DOCUMENTS

| 4,629,464 A | 12/1986 | Takata |
| 4,798,585 A | 1/1989 | Inoue |

(Continued)

FOREIGN PATENT DOCUMENTS

| DE | 19738052 A1 | 3/1999 |
| EP | 0760687 A1 | 3/1997 |

(Continued)

*Primary Examiner* — David H Willse
(74) *Attorney, Agent, or Firm* — Fitch, Even, Tabin & Flannery LLP

(57) ABSTRACT

Implant devices for implantation within an intervertebral space are provided, together with methods and tools for use therewith. Implant devices of the present invention include an implant body formed of a synthetic bone substitute material, such as a nanocrystalline calcium phosphate material. The implant body and the methods and tools used therewith are configured to optimize strength and stability of the implant, minimize areas of stress concentration in the implant body and promote bone growth through the implant body and fusion of the vertebra.

11 Claims, 18 Drawing Sheets

(51) Int. Cl.
*A61L 27/12* (2006.01)
*A61F 2/30* (2006.01)
*A61F 2/28* (2006.01)

(52) U.S. Cl.
CPC ............... *A61F 2002/30677* (2013.01); *A61F 2002/30892* (2013.01); *A61F 2002/30968* (2013.01); *A61F 2002/3097* (2013.01); *A61F 2002/4627* (2013.01); *A61F 2002/4628* (2013.01); *A61F 2002/4629* (2013.01); *A61F 2210/0004* (2013.01); *A61F 2230/0082* (2013.01); *A61F 2310/00023* (2013.01); *A61F 2310/00796* (2013.01); *A61L 27/12* (2013.01); *A61L 2400/12* (2013.01); *A61L 2430/38* (2013.01); *A61F 2310/00293* (2013.01)

(56) References Cited

U.S. PATENT DOCUMENTS

| | | |
|---|---|---|
| 4,878,914 A | 11/1989 | Miwa |
| 5,011,495 A | 4/1991 | Hollinger |
| 5,152,791 A | 10/1992 | Hakamatsuka |
| 5,171,327 A | 12/1992 | Koch |
| 5,306,307 A | 4/1994 | Senter |
| 5,306,309 A | 4/1994 | Wagner |
| 5,514,180 A | 5/1996 | Heggeness |
| 5,522,894 A | 6/1996 | Draenert |
| 5,531,794 A | 7/1996 | Takagi |
| 5,645,596 A | 7/1997 | Kim |
| 5,669,909 A | 9/1997 | Zdeblick |
| 5,980,572 A | 11/1999 | Kim |
| 5,989,289 A | 11/1999 | Coates |
| 6,037,519 A | 3/2000 | McKay |
| 6,039,762 A | 3/2000 | McKay |
| 6,149,688 A | 11/2000 | Brosnahan |
| 6,245,108 B1 | 6/2001 | Biscup |
| 6,261,587 B1 | 7/2001 | Usala |
| 6,277,149 B1 | 8/2001 | Boyle |
| 6,280,478 B1 | 8/2001 | Richter |
| 6,302,913 B1 | 10/2001 | Ripamonti |
| 6,312,472 B1 | 11/2001 | Hall |
| 6,344,061 B1 | 2/2002 | Leitao |
| 6,346,123 B1 | 2/2002 | McKay |
| 6,350,462 B1 | 2/2002 | Hakamatsuka |
| 6,503,279 B1 | 1/2003 | Webb |
| 6,527,810 B2 | 3/2003 | Johnson |
| 6,758,849 B1 | 7/2004 | Michelson |
| 6,758,862 B2 | 7/2004 | Berry |
| 6,776,860 B2 | 8/2004 | Arai |
| 6,843,805 B2 | 1/2005 | Webb |
| 6,846,327 B2 | 1/2005 | Khandkar |
| 6,858,041 B2 | 2/2005 | Richter |
| 6,887,272 B2 | 5/2005 | Shinomiya |
| 6,923,810 B1 | 8/2005 | Michelson |
| 6,986,789 B2 | 1/2006 | Schultz |
| 6,987,136 B2 | 1/2006 | Erbe |
| 6,991,653 B2 | 1/2006 | White |
| 7,033,394 B2 | 4/2006 | Michelson |
| 7,044,972 B2 | 5/2006 | Mathys |
| 7,060,073 B2 | 6/2006 | Frey |
| RE39,196 E | 7/2006 | Ying |
| 7,083,749 B2 | 8/2006 | Lin |
| 7,087,540 B2 | 8/2006 | Heide |
| 7,118,598 B2 | 10/2006 | Michelson |
| 7,122,057 B2 | 10/2006 | Beam |
| 7,135,042 B2 | 11/2006 | Stoll |
| 7,169,183 B2 | 1/2007 | Liu |
| 7,223,289 B2 | 5/2007 | Trieu |
| 7,226,480 B2 | 6/2007 | Thalgott |
| 7,230,039 B2 | 6/2007 | Trieu |
| 7,238,203 B2 | 7/2007 | Bagga |
| RE41,584 E | 8/2010 | Ying |
| 8,002,837 B2 | 8/2011 | Stream |
| 2002/0082700 A1 | 6/2002 | Bianchi |
| 2002/0115742 A1 | 8/2002 | Trieu |
| 2003/0003127 A1 | 1/2003 | Brown |
| 2004/0052829 A1 | 3/2004 | Shimp |
| 2004/0167637 A1 | 8/2004 | Biscup |
| 2004/0249471 A1 | 12/2004 | Bindseil |
| 2005/0015154 A1 | 1/2005 | Lindsey |
| 2005/0031704 A1 | 2/2005 | Ahn |
| 2005/0065604 A1 | 3/2005 | Stoll |
| 2005/0177237 A1 | 8/2005 | Shappley |
| 2005/0177238 A1 | 8/2005 | Khandkar |
| 2005/0177245 A1 | 8/2005 | Leatherbury |
| 2005/0196420 A1 | 9/2005 | Zucherman |
| 2005/0228498 A1 | 10/2005 | Andres |
| 2005/0251267 A1 | 11/2005 | Winterbottom |
| 2005/0267587 A1 | 12/2005 | Lin |
| 2005/0267588 A1 | 12/2005 | Lin |
| 2005/0267589 A1 | 12/2005 | Lin |
| 2005/0281856 A1 | 12/2005 | McGlohorn |
| 2006/0149388 A1 | 7/2006 | Smith |
| 2006/0247772 A1 | 11/2006 | McKay |
| 2007/0032568 A1 | 2/2007 | Lin |
| 2007/0162128 A1 | 7/2007 | DeRidder |
| 2008/0071372 A1 | 3/2008 | Butler |
| 2008/0306596 A1* | 12/2008 | Jones et al. ............. 623/17.16 |
| 2009/0099661 A1 | 4/2009 | Bhattacharya |

FOREIGN PATENT DOCUMENTS

| | | |
|---|---|---|
| WO | 9717285 A1 | 5/1997 |
| WO | 9920208 A1 | 4/1999 |
| WO | 2007121457 A1 | 10/2007 |
| WO | 2008140551 A2 | 11/2008 |

* cited by examiner

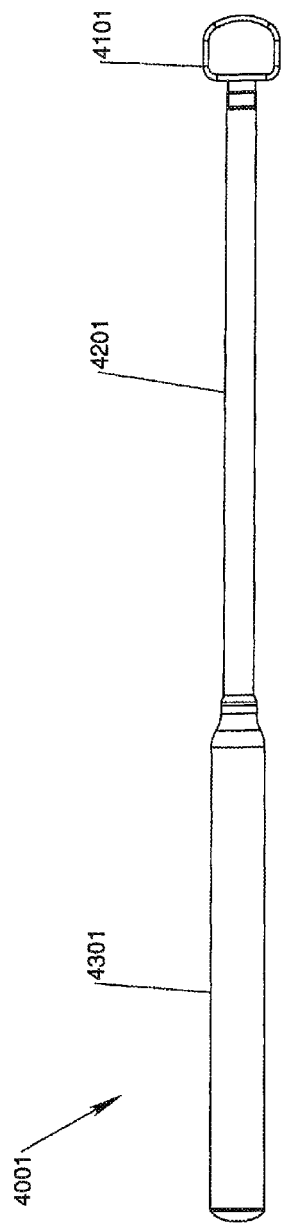
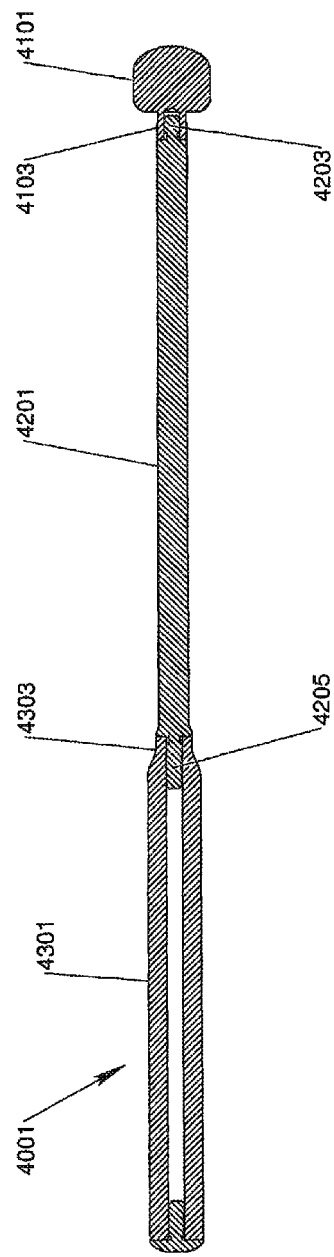
Fig. 7 A
Fig. 7 B

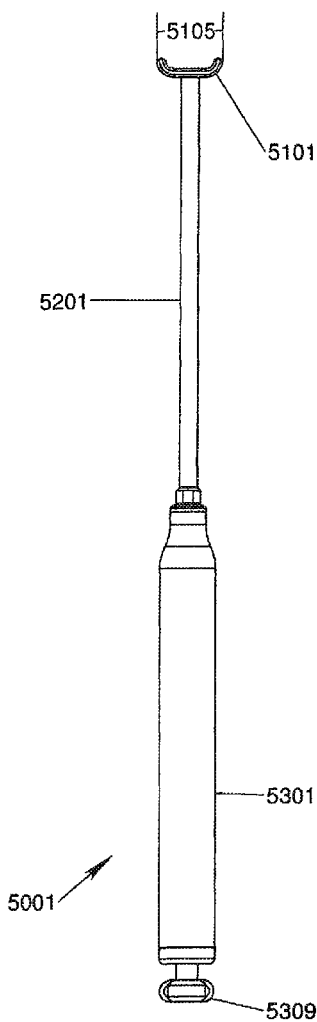
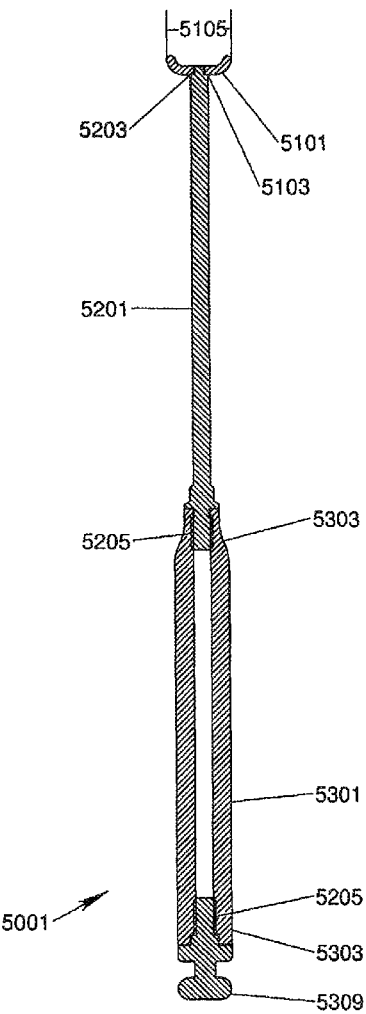
Fig. 9 A          Fig. 9 B

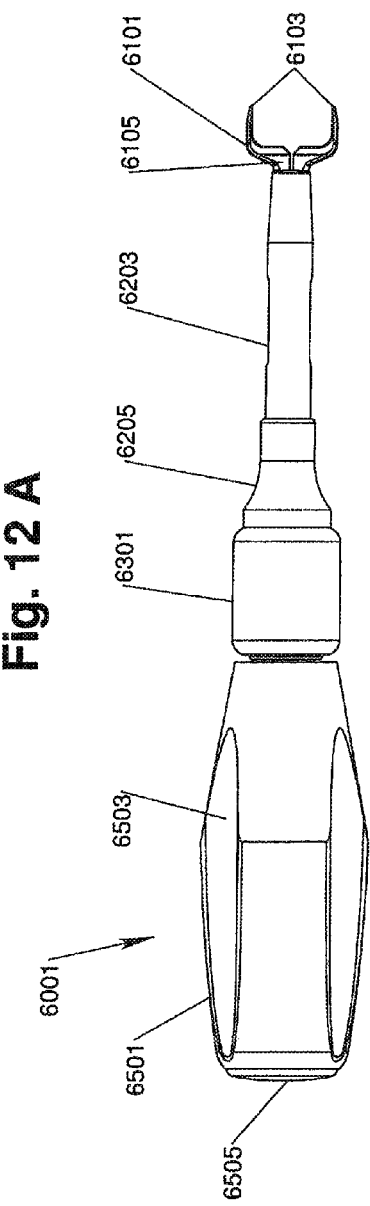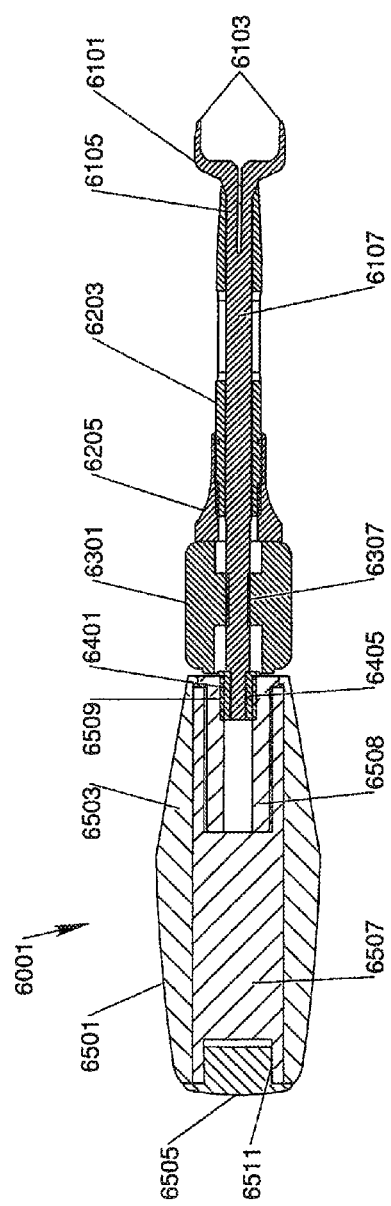

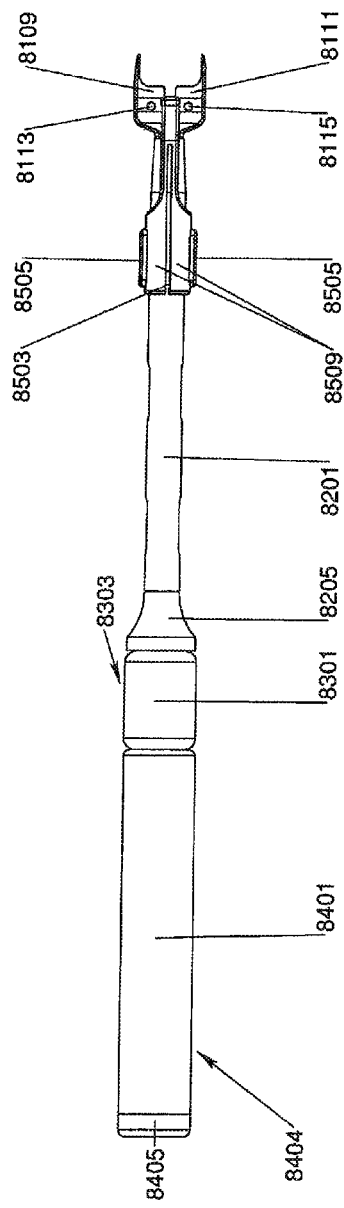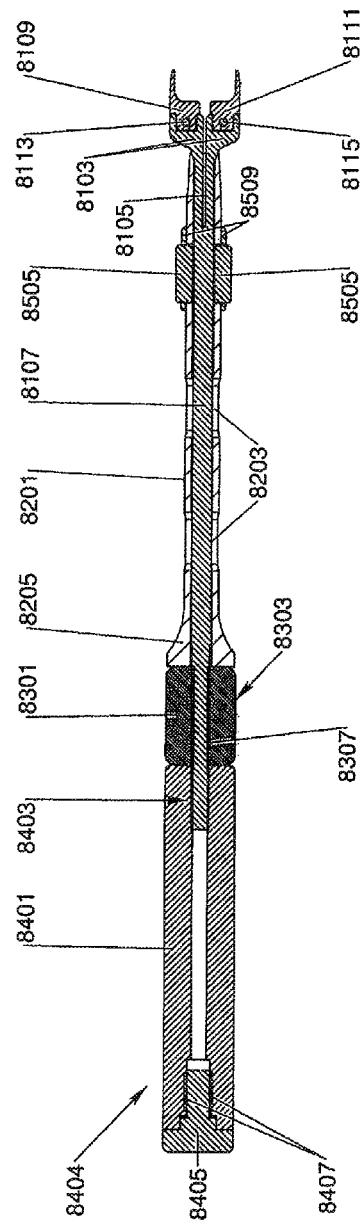
Fig. 17A
Fig. 17B

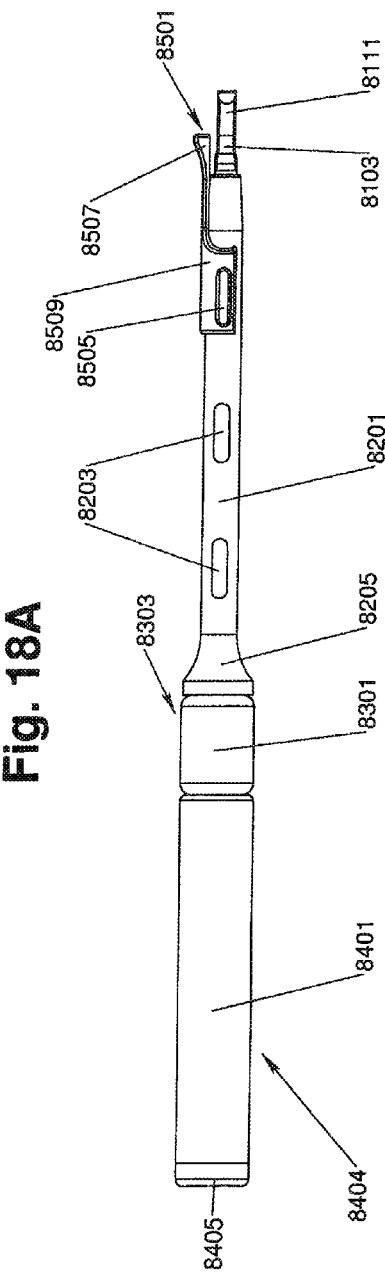
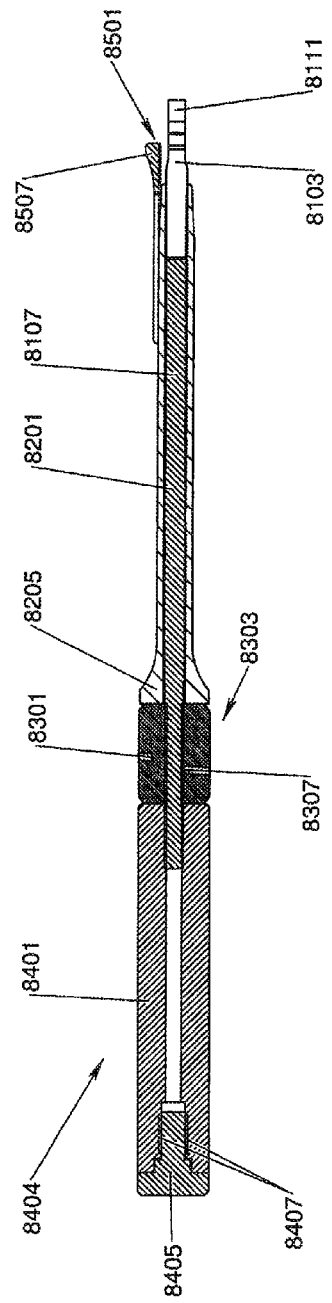
Fig. 18A
Fig. 18B

INTERVERTEBRAL IMPLANT DEVICES FOR SUPPORTING VERTEBRAE AND DEVICES AND METHODS FOR INSERTION THEREOF

CROSS-REFERENCE TO RELATED APPLICATIONS

This application is a continuation of prior U.S. application Ser. No. 12/417,356, filed Apr. 2, 2009, now U.S. Pat. No. 8,470,040 B2, issued Jun. 25, 2013, which claims the benefit of U.S. Provisional Application No. 61/041,893, filed Apr. 2, 2008, and U.S. Provisional Application No. 61/042,139, filed Apr. 3, 2008, which are all hereby incorporated herein by reference in their entirety.

FIELD OF THE INVENTION

This invention pertains generally to implantable medical devices and, in particular, to implantable devices for intervertebral fusion and/or immobilization.

BACKGROUND OF THE INVENTION

Many people develop back pain during the course of their life due to traumatic injury, disease, or genetic defect. Typically, the patients' intervertebral discs, which support the spine, are damaged, causing the discs to bulge or herniate. The disc bulge then impinges on the nerves of the spine and cause back pain. Surgeons often perform a discectomy to trim the disc bulge to alleviate back pain. However, the discectomy may structurally weaken the disc and often leads to subsequent structural failure of the disc due to wear and aging, once again causing impingement on the nerves of the spine and cause back pain. Surgical implantation of a medical implant device to structurally support and separate the vertebrae may become desirable to end debilitating back pain and allow patients to regain normal life activities.

One currently accepted practice is to use natural bone from the patient (i.e., autograft) or cadaver bone donated by organ donors (i.e. sterilized allograft), as a material to structurally support and separate the vertebrae. While natural bone implants advantageously promote bone growth and fusion at the implant site, the use of natural bone can be problematic because of the potential for structural failure of the implant, rejection of the implant by the patient, and the risk of infection.

In particular, failure of the bone graft implant may be caused by non-viability of the bone graft material, which allows for accumulation of structural micro-damage. In addition, the quality of the bone graft greatly depends on the health and age of the bone donor, which results in highly variable quality in bone graft. Failure of the implant can also result from rejection of the implant by the patient's immune system. In addition, the risk of infection from cadaver bone creates many attendant costs of mitigation. The potential for implant failure, rejection, and/or infection may necessitate numerous painful revision surgeries.

In view of the problems associated with natural bone implants, vertebral body replacement devices ("VBRs") are often made of strong and non-brittle biocompatible materials, such as carbon fiber, titanium, and/or materials of the polyaryletherketone family, including, for example, PEEK (polyetheretherketone), PAEK (polyaryletherketone), PEK (polyetherketone), PEKK (polyetherketoneketone), PEKEKK (polyetherketoneetherketoneketone), PEEKK (polyetheretherketoneketone), and PAEEK (polyaryletheretherketone), and any combination thereof.

VBRs commonly have generally annular bodies including relatively large, central throughbores in which bone graft material can be packed to encourage bony ingrowth through the throughbore. Other smaller openings, apertures and/or channels can also be provided in the implant for allowing bone ingrowth and/or for cooperating with corresponding engagement members of an insertion tool for inserting the VBR between vertebrae. In this regard, during VBR insertion there generally are very high forces generated at the interface between the engagement members of the insertion tool and the surfaces about the VBR body openings in which the engagement members are fit. VBRs formed of a material such as PEEK are advantageously strong and ductile to minimize damage to the implant body during insertion. However, such materials are not bioresorbable and do not allow bone growth through the implant body itself. Moreover, should a revision surgery be required, the implant must be removed with particular care given to ensure there is not remaining debris.

Bioactive bioceramic materials, such as hydroxyapatite (HA) and tricalcium (TCP) phosphate are attractive and widely utilized materials for orthopedic and dental implants. A "bioactive" material is one that elicits a specific biological response at its surface, which results in a beneficial biological and chemical reaction with the surrounding tissue. These reactions lead to chemical and biological bonding to the tissue at the interface between tissue and the bioactive implant, rather than mere ingrowth of tissue into pores of the implant, which only provide mechanical fixation. HA has been of particular interest in orthopedic and dental application because the composition closely resembles native bone mineral and is inherently bioactive and osteoconductive. However, because such calcium phosphate bioceramic implants have low reliability under tensile loads, such materials have generally only been used as powders, or as small, unloaded implants such as in the middle ear, dental implants with reinforcing metal posts, coatings on metal implants, low-loaded porous implants where bone growth acts as a reinforcing phase, and as the bioactive phase in a composite implant.

Thus, it would be advantageous to provide an implant device for implantation in the intervertebral space between vertebral bodies for supporting and/or spacing apart the vertebral bodies and promoting bone growth and fusion therebetween and/or immobilization thereof. It would further be advantageous to provide such an implant device formed of a material that provides the strength and stability, while also being bioresorbable and promoting bone growth therein. The present invention may be used to fulfill these needs, as well as other needs and benefits, as will be apparent from the following description of embodiments of the present invention.

SUMMARY OF THE INVENTION

In accordance with one aspect of the invention, an implant device for implantation within an intervertebral space between adjacent vertebrae is provided. The implant device includes an implant body preferably formed of a synthetic bone substitute material that is desirably bioresorbable and osteoconductive, but is less ductile than materials typically used for intervertebral implants (such as PEEK, for example). Hence, the implant body and the methods and tools for implanting the device are configured to optimize the physical characteristics of the device and the material used and minimize stress concentration in the implant body.

In one form, the implant body has a smooth, continuous annular wall defining an inner void and vertebral body gripping structure configured for minimizing locations of stress concentration in the implant body. This allows for optimized strength and stability while also promoting bone growth through the implant body and fusion of the vertebrae. With the smooth, continuous annular wall, the implant body lacks any openings, throughbores, channels, cut-outs, and/or sharp corners therein that can provide areas on the implant body in which stress may be concentrated. Preferably, the only opening in the implant body is the inner void or throughbore that extends through the implant body along a central axis that is generally aligned with the compressive forces that the implant will bear once inserted between adjacent vertebrae.

In another form, additional small openings and/or throughbores can be formed in the annular wall of the implant body as long as they do not tend to create areas of stress concentration (for example, those that extend in the axial direction and preferably include only smoothly curved surfaces extending thereabout). Like the inner void, these other openings can be filled with a material for promoting bone growth, such as graft material. Alternatively, these smaller openings can simply be left open for bone growth therethrough.

In another form, the vertebral body gripping structure is configured for securely engaging the corresponding upper and lower adjacent vertebrae while minimizing areas of stress concentration in the implant body. The gripping structure is preferably in the form of raised ridges defined by alternating peaks and troughs, with the peak summits and the troughs preferably being rounded or curved, without any sharp angles or points.

In accordance with another aspect of the invention, the implant body is preferably formed of nanocrystalline hydroxyapatite (HA) and/or tricalcium phosphate (TCP) material or other bioresorbable synthetic bone substitute. The bioresorbable nature of the material minimizes the need for any subsequent revision surgeries. Furthermore, the material is advantageously osteoconductive (i.e., promotes bone growth) and allows living bone growth into the implant body, thus creating a more secure connection between the implant and the adjacent bone.

One significant advantage of the use of synthetic bone material such as HA or TCP is the low likelihood of rejection and subsequent complications as compared to natural bone. The use of synthetic bone reduces the risk of complications from subsequent surgeries, produces improved surgical results, and reduces the risk of pain to the patient. Another advantage of synthetic bone as a substitute for natural bone is the substantial elimination of the risk of infection passed by a cadaver bone and the corresponding costs in mitigating the risk of infection.

In one preferred form, the implant device is constructed of nanocrystalline calcium phosphate compounds that are densely packed to form a durable structure. In one form, implant devices according to the present invention may be formed of a nanocrystalline HA such as described in U.S. Pat. No. RE 39,196, which is hereby incorporated herein in its entirety. This nanocrystalline HA has a very small crystal size, allowing the crystals to be tightly packed so that articles made thereof approach 100% theoretical density. As a result, the nanocrystalline HA, when formed into an implant, provides superior structural performance compared to other hydroxyapatites. In another form, implant devices of the present invention are formed of nanocrystalline TCP, such as described in U.S. Patent Application Publication No. 2005/0031704, which is hereby incorporated herein in its entirety. The nanocrystalline TCP provides greater reliability and better mechanical properties than other forms of tricalcium phosphate. In yet another form, the implant device is constructed of a nanocrystalline calcium phosphate material such as NANOSS™, an engineered synthetic bone platform utilizing nanotechnology.

The density and strength of these preferred nanocrystalline materials substantially reduce the risk of structural failure as compared to other synthetic bone implants. Additionally, the structure of the implant device and the procedures for its implantation and use are optimized to accommodate the unique structural capabilities of these nanocrystalline calcium phosphate materials. In particular, the implant body's shape (including, for example, the smooth, continuous annular wall and curved gripping structure) is preferably configured to minimize any stress concentration points in the nanocrystalline calcium phosphate material. Additionally, the wall thickness is configured to provide desired structural strength for withstanding compressive and torsional forces while maximizing the area available for introducing biologic products to encourage bone growth and fusion. The use of dense forms of HA, TCP or similar artificial bone materials allows for the manufacture of an implantable device that is a practical and viable alternative to natural bone that eliminates the risk of infection from donors and risk of rejection by the patient.

Additional advantages and features of the invention will become apparent from the following description and attached claims taken in combination with the accompanying drawings.

BRIEF DESCRIPTION OF DRAWINGS

FIGS. 7A and 7B are top plan and top cross-sectional views, respectively, of the trial spacer tool of FIG. 6;

FIGS. 9A and 9B are top plan and top cross-sectional views, respectively, of the tamp device of FIG. 8;

FIGS. 12A and 12B are top plan and top cross-sectional views, respectively, of the implant insertion tool of FIG. 10;

FIGS. 17A and 17B are top and top cross-sectional views, respectively, of the implant insertion tool of FIG. 15

FIGS. 18A and 18B are side and side cross-sectional views, respectively, of the implant insertion tool of FIG. 15.

DETAILED DESCRIPTION OF THE PREFERRED EMBODIMENTS

With reference to FIGS. 1, 2A, 2B, 3, 4, 5A and 5B, in accordance with one aspect of the invention, an implant device 1000 has an implant body 1001 that is configured to be implanted in the intervertebral space between adjacent vertebrae. The implant body 1001 preferably has a generally rectangle-shaped, annular wall 1051 including an anterior wall portion 1005, a posterior wall portion 1003, and opposing side wall portions 1031, 1033. The annular wall 1051 defines upper and lower vertebral engaging surfaces 1019, 1021 and is disposed about a central void or throughbore 1009 extending therebetween, the throughbore 1009 being configured for accepting biologic materials, such as bone graft and/or bone void fillers therein.

A vertical axis 1001A of the implant body 1001 extends through the upper and lower vertebral engaging surfaces 1019, 1021, generally parallel to the throughbore 1009. An anterior-posterior axis 1001B of the implant body 1001 extends through the center of the anterior and posterior wall portions 1005, 1003. A lateral axis 1001C of the implant body extends through the center of opposing side walls 1031, 1033.

The implant device 1000 is preferably composed of a biocompatible, synthetic bone substitute material, such as a nanocrystalline HA and/or TCP, that is desirably bioresorbable and osteoconductive, but is less ductile than materials typically used for these types of intervertebral implants (such as PEEK, for example). Thus, the structure of implant device 1000 and methods and tools for implanting the device are configured to optimize the physical characteristics of the device and the material used.

Figure 1:
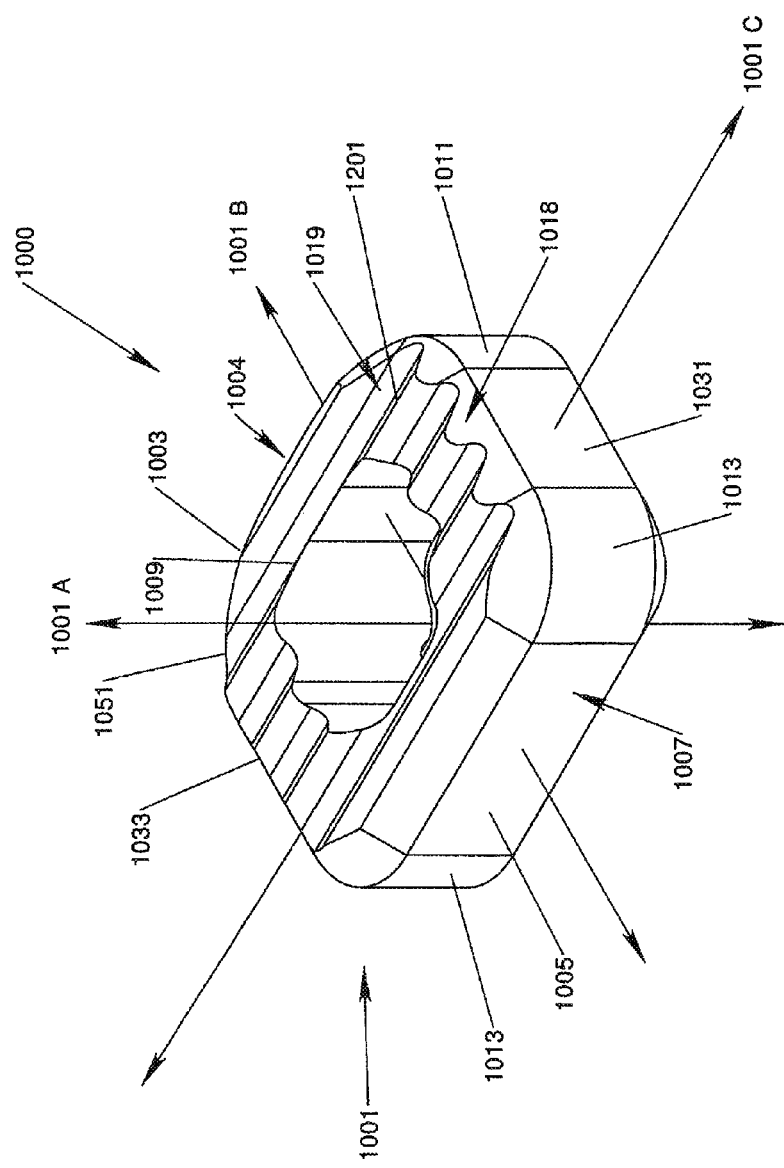
FIG. 1 is a perspective view of an implant device in accordance with one aspect of the invention.
Figure 2A:
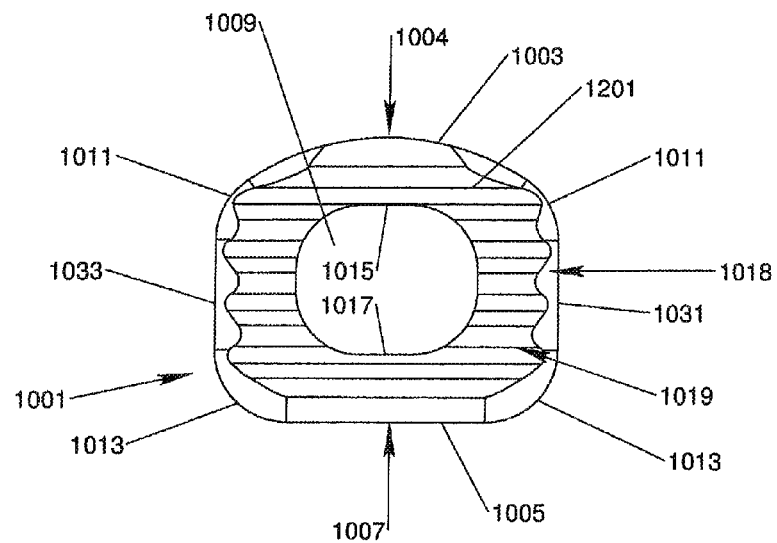
FIG. 2A is a top plan view of the implant device of FIG. 1.
Figure 2B:
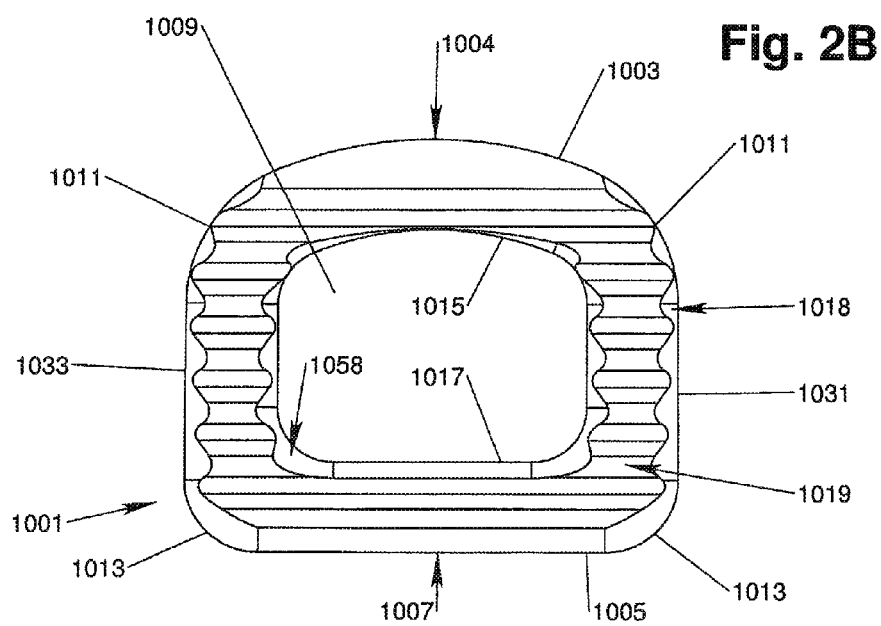
FIG. 2B is a top plan view of the implant device of FIG. 1 with an additional chamfered surface.

As illustrated, annular wall 1051 of implant body 1001 is preferably smooth and continuous, without any openings, apertures, channels, sharp corners or the like therein. An inner surface of the annular wall 1051, including a curved posterior inner wall portion 1015 and a curved anterior inner wall portion 1017, is likewise preferably smooth and continuous. As seen in FIGS. 1, 2A and 2B, a posterior surface 1004 of the posterior wall portion 1003 of the annular wall 1051 of the implant body 1001 has a generally smooth convexly curved shape configured to conform generally to the shape of the vertebrae of the spine. Upon insertion of the implant body 1001, the posterior wall portion 1003 of the implant body 1001 is positioned at the posterior region of the vertebrae. The curved shape of the posterior surface 1004 of posterior wall portion 1003 assists in distracting tissue during insertion of the implant body 1001.

Figure 3:
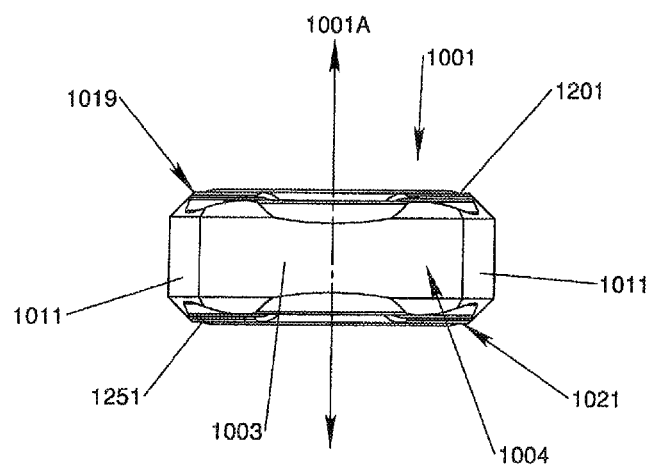
FIG. 3 is a posterior end view of the implant device of FIG. 1.
Figure 4:
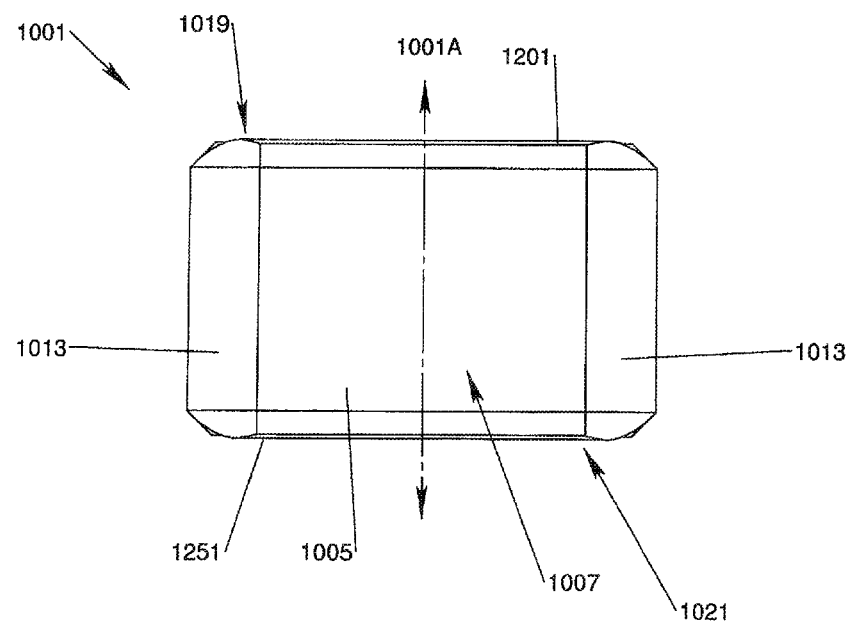
FIG. 4 is an anterior end view of the implant device of FIG. 1.

As seen best in FIGS. 2A, 2B and 3, the posterior wall portion 1003 of the annular wall 1051 extends around the perimeter of the implant body 1001 to opposing side wall portions 1031, 1033. Likewise, anterior wall portion 1005 extends to opposing side wall portions 1031, 1033. Upon insertion of the implant 1001, the anterior wall portion 1005 of the implant body 1001 is positioned at the anterior region of the vertebrae. As seen in FIG. 4, in one form, the anterior wall portion 1005 has a substantially flat anterior surface 1007. The flat anterior surface 1007 provides a bearing surface for an insertion tool, such as insertion tool 6001 configured to engage the implant body 1001 and forcibly drive the implant body 1001 into position. In another form, the anterior surface may be curved.

Implant body 1001 may have a number of different heights and/or footprint sizes to best accommodate the patient's individual physical characteristics. As will be readily understood by those of ordinary skill in the art, while preferred implant devices are described herein having three different sizes of footprints and varying heights, other footprint sizes and heights are contemplated. In one form, the implant device 1000 measures about 10 mm (in the posterior-anterior direction along axis 1001B)×12 mm (in the lateral direction along axis 1001C). In another form, the implant device measures about 12 mm×14 mm. In still another form, the implant device measures about 14.5 mm×17 mm. For any given footprint size, a number of different implant heights may be provided in order to maintain a desired spacing between vertebrae.

Preferably, the height of the implant device 1000 ranges from about 5 mm to about 11 mm. The descriptions herein are generally applicable to the implant body 1001 of the present invention regardless of the footprint size and/or height.

The thickness of the annular wall 1051, including the posterior wall portion 1003 and the anterior wall portion 1005, are selected to withstand the multiple forces applied to the implant body during insertion and within the intervertebral space, including compressive loads, torsional loads, insertion loads, expulsion loads, and subsidence loads. In accordance with one aspect, the implant body 1001 is designed to support static loading in the lumbar region of the spine, as the lumbar region supports the entire torso and therefore subjects the implant body 1001 to the most demanding load conditions. However, the implant body 1001 is preferably configured to be implanted in other areas of the spine as well, such as the cervical and thoracic regions. Further, the posterior wall portion 1003 and anterior wall portion 1005 are configured to meet the fatigue strength requirements of axial and torsional loading for a typical patient. Preferably, the implant body 1001 complies with U.S. Food and Drug Administration (FDA) regulations and ASTM F 2077-03. Preferably, the implant body 1001 can withstand axial loading of at least about 5000N, more preferably, at least about 6500N, and most preferably, at least about 10,000N. The implant body 1001 preferably has a compressive strength of at least about 80 MPa, more preferably, at least about 100 MPa, and most preferably, at least about 120 MPa.

The thickness of the annular wall 1051, including the posterior wall portion 1003 and the anterior wall portion 1005, is preferably optimized to balance the structural strength required to withstand the potential compressive loads against the desire to maximize the size of the throughbore 1009 to accept bone void fillers therein to promote bone growth. Minimizing the thickness of the posterior wall portion 1003 and anterior wall portion 1005 increases the area of the throughbore 1009. As the size of the throughbore 1009 increases the amount of biological products (i.e., bone graft and/or bone void fillers), which can be received by the throughbore 1009 increases. The thickness of the posterior wall portion 1003, the anterior wall portion 1005 and the side walls 1031, 1033 may be consistent or may vary from wall to wall. Preferably, the thickness of each wall is in the range of about 2 mm to about 3.5 mm, more preferably, about 2.3 mm to about 3.2 mm.

Preferably, the ratio of the radius of the throughbore 1009 to the wall thickness is optimized for providing the desired structural strength while maximizing the size of the throughbore 1009. As illustrated in FIGS. 2A and 2B, "the radius" of throughbore 1009 refers to the radius of the curved corner portions of posterior inner wall portion 1015 and anterior inner wall portion 1017. Preferably, the radius of the throughbore 1009 is in the range of about 1.75 mm to about 2.5 mm, more preferably, about 1.9 mm to about 2.3 mm. Thus, the ratio of the radius of the throughbore 1009 to the wall thickness is preferably about 60-98%. In one form, the ratio of the radius of throughbore 1009 to wall thickness that is about 60.8%. In another form the ratio of the radius of throughbore 1009 to wall thickness is about 81.08%. In yet another form, the ratio of the radius of throughbore 1009 to wall thickness is about 96.7%. In yet another form, the ratio of the radius of the throughbore 1009 to wall thickness varies from wall to wall.

The concentration of stress in the implant body depends primarily on the geometry of the device rather than the material itself. An implant body can be configured to minimize the concentration of stress therein, for example, by eliminating corners or cut-out portions. However, the overall effect of stress concentrations on the structural integrity of the implant depends on the compressive strength, brittleness, and other properties of the material that makes up the implant. Therefore, structural shape of the implant body 1001 is configured to include smooth, continuous curve surfaces to minimize any stress concentration points.

In a preferred embodiment, the shape of the posterior wall portion 1003 and anterior wall portion 1005 of the annular wall 1051 of the implant body 1001 are configured to provide gradual changes in shape yet maintain the desired thicknesses of the posterior wall portion 1003 and anterior wall portion 1005 best seen in FIGS. 2A and 2B.

Anterior corner portions 1013, where the anterior wall portion 1005 of the implant body 1001 joins the opposing side walls 1031, 1033 and posterior corner portions 1011, where the posterior wall portion 1003 joins the opposing side walls 1031, 1033 are smoothly curved to minimize stress concentration therein. The posterior surface 1004 of the posterior wall portion 1003, the curved posterior inner wall portion 1015 and the curved anterior inner wall portion 1017 are also configured to minimize stress concentration.

The upper and lower vertebral engaging surfaces 1019, 1021 are also preferably configured to minimize areas of stress concentration. As can be seen, for example, in FIGS. 5A and 5B, in one form, upper and lower vertebral engaging surfaces 1019, 1021 are preferably slanted with respect to each other so as to provide a generally wedge-shaped implant body 1001.

The spine does not have a straight axis throughout its length and has varying curvature known as a lordosis. The spinal lordosis results in the planes defined by adjacent vertebrae not being necessarily parallel. Thus, it is preferred that the shape of implant body 1001 defined by slanted upper and lower vertebral engaging surfaces 1019, 1021 has a degree of lordosis that generally corresponds to the natural lordosis of the spine.

As illustrated, the upper vertebral engaging surface 1019 has a line of lordosis 1271 extending along the upper vertebral engaging surface in the posterior-anterior direction. Likewise, the lower vertebral engaging surface 1021 has a line of lordosis 1273 extending along the lower vertebral engaging surface in the posterior-anterior direction. The line of lordosis 1271 of the upper vertebral engaging portion 1019 intersects the anterior-posterior axis 1001B of the implant body 1001 at an angle x. While the line of lordosis 1273 of the lower vertebral engaging portion 1021 intersects the anterior-posterior axis 1001B of the implant body 1001 at an angle y.

Figure 5:
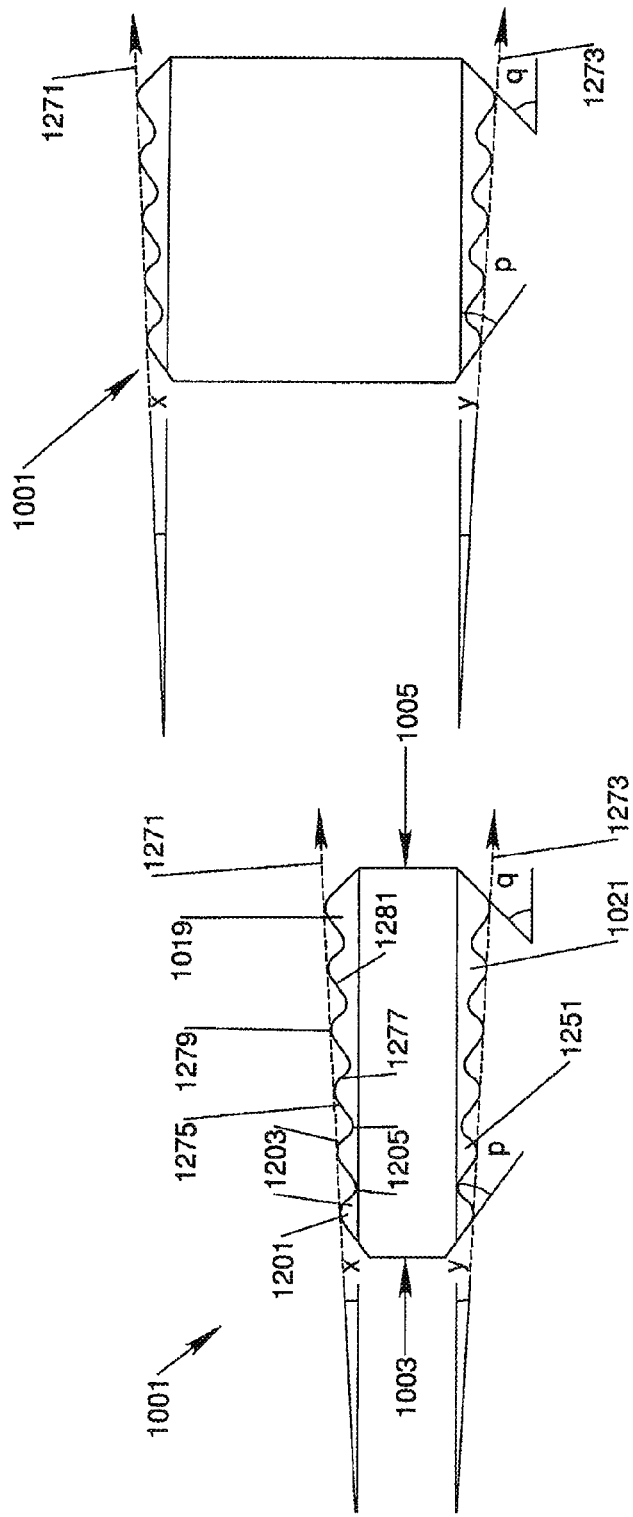
FIGS. 5A and 5B are side views of two implant devices of FIG. 1 having different heights.

The implant body 1001 may be configured to provide any desired degree of lordosis. In preferred form, angle x is about 3 degrees and angle y is about 3 degrees giving the implant body 1001 a degree of lordosis of about 6 degrees. The angles x and y need not be identical, as long as they cooperate to provide the desired degree of lordosis. As can be seen in FIGS. 5A and 5B, the angles x and y may be present regardless of the height of the implant. In an alternative form, the upper and lower vertebral engaging surfaces 1019, 1021 are substantially parallel to one another (i.e., the angles x and y are 0 degrees.)

Providing the implant body 1001 with a proper degree of lordosis advantageously ensures even loading of the upper vertebral engaging surface 1019 and the lower vertebral engaging surface 1021 and maximum structural strength of the implant body 1001. The proper degree of lordosis also ensures even compression of the vertebrae on the implant body 1001 to prevent slippage or expulsion of the implant. Finally, the degree of lordosis also allows for relative ease of insertion of the implant body 1001 by providing a tapered wedge shape.

According to another aspect, the upper and lower vertebral engaging surfaces 1019, 1021 preferably have upper and lower gripping features 1201, 1251 formed thereon that are configured to engage and grip the adjacent vertebral bodies. The upper gripping features 1201 and lower gripping features 1251 preferably promote friction between the implant body 1001 and adjacent vertebrae, i.e. gripping, to keep the implant body 1001 from being expelled after implantation. The upper gripping features 1201 and lower gripping features 1251 also preferably resist migration of the implant body 1001 and serve to immobilize the adjacent vertebrae relative to each other and the implant body 1001, thereby resisting expulsion of the implant body 1001 when subjected to a force, such as a lateral force from the bending of the patient's back, that could otherwise cause the implant to slip out of the implanted position on the vertebrae.

Preferably, the upper and lower gripping features 1201, 1251 are configured to both securely engage and grip the adjacent vertebrae to facilitate fusion between the vertebrae and the implant body 1001 and to minimize stress concentration therein. As shown, for example, in FIGS. 5A and 5B, the upper and lower gripping features 1201, 1251 have a generally grooved surface created by alternating curved peaks 1203 and curved troughs 1205 extending generally parallel to the lateral axis 1001C of the implant body as best seen in FIGS. 1, 2A and 2B. As illustrated, the peaks 1203 and troughs 1205 are preferably configured to promote friction between the implant body 1001 and adjacent vertebrae but are advantageously curved, without any sharp edges and/or points to minimize stress concentration thereon.

Figure 14:
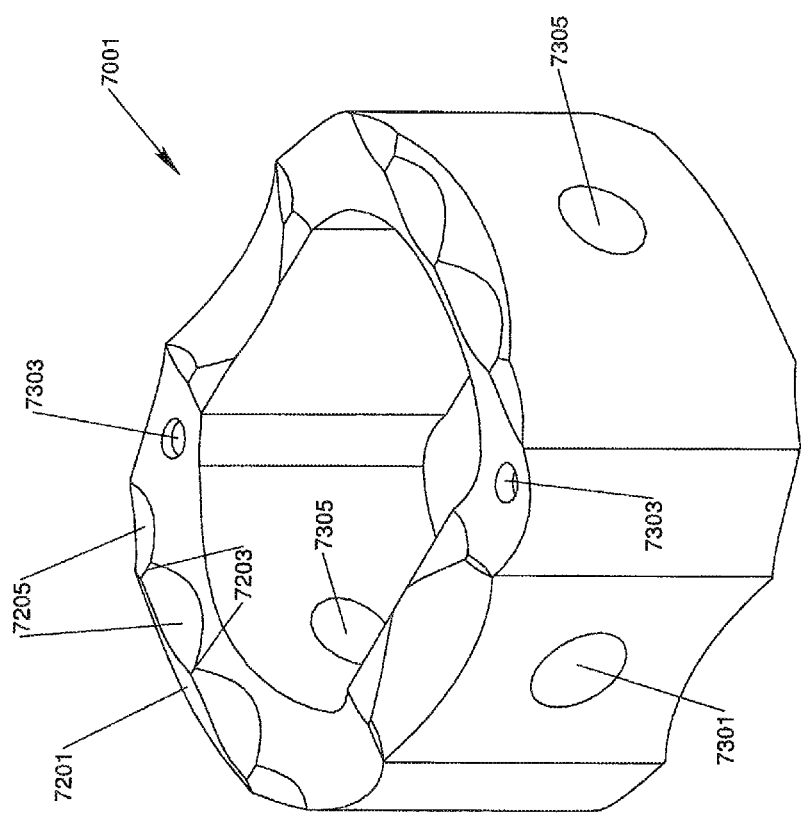
FIG. 14 is a perspective view of a prior art implant design.
Figure 15:
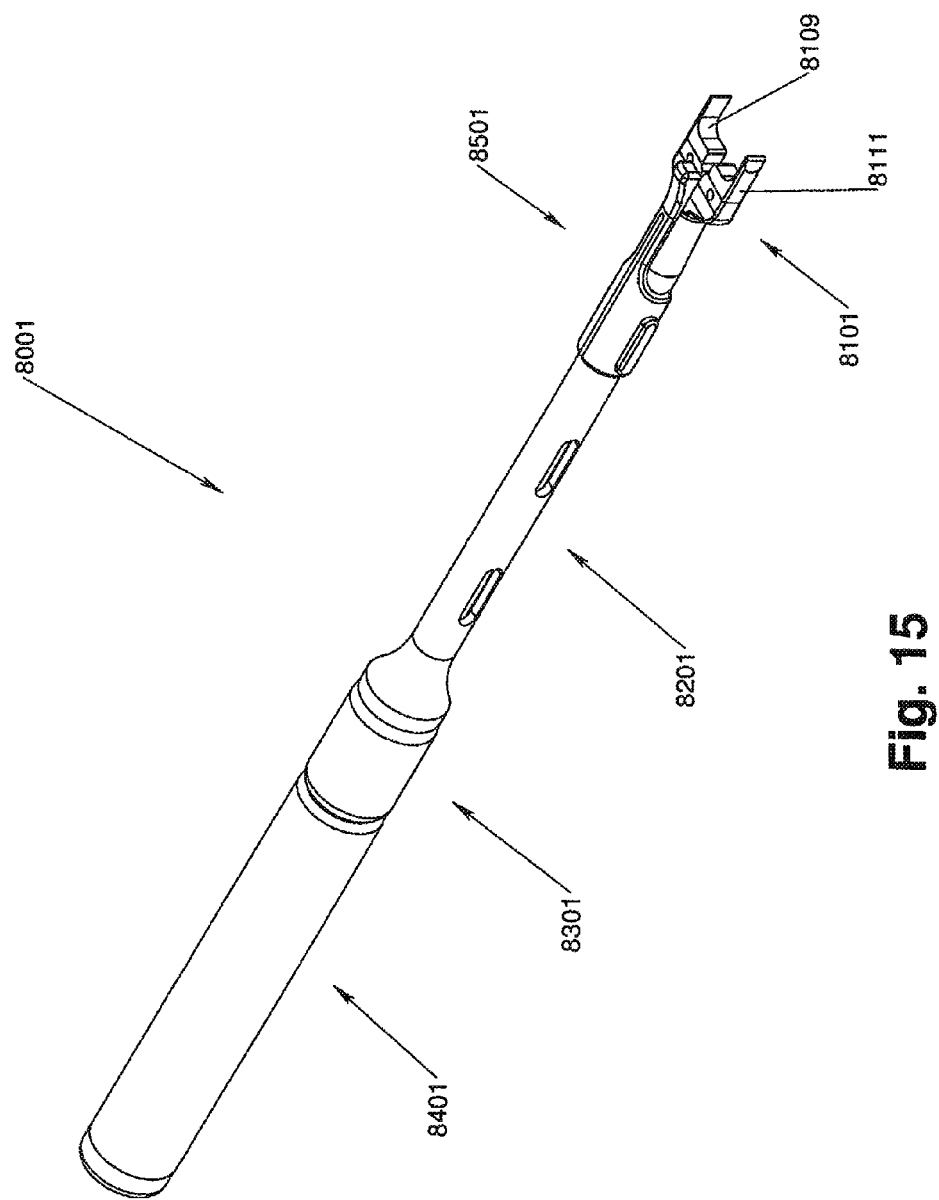
FIG. 15 is a perspective view of an implant insertion tool in accordance with another aspect of the invention.

In contrast, conventional VBRs, such as prior art implant 7001 shown in FIG. 14 (and described in U.S. Patent Application Publication 2006/0129238 A1), have gripping features 7201 that have sharp edges on the peaks 7203 and troughs 7205 to promote greater friction. The use of rounded gripping features 1201, 1251 promotes the desired friction while advantageously minimizing stress concentration by gripping with a rounded structure having a more durable surface.

The peaks 1203 of gripping features 1201, 1251 are preferably uni-directional so as to assist insertion, resist expulsion of the implant body 1001, and minimize insertion impact stress on the implant body. More specifically, each peak 1203 has a leading portion 1275 facing the posterior wall portion 1003 (i.e., facing the direction of insertion of the implant body 1001), a curved summit 1279, and a trailing portion 1277 facing the anterior wall portion 1005 of the implant body 1001. The radii of the curved summits 1279 (in one form, preferably about 0.5 mm) and the curved troughs 1205 (in one form, preferably about 0.4 mm) are centered on the line of lordosis 1271, 1273. Thus, as shown in FIG. 5A, the leading portion 1275 includes a generally flat portion 1281 disposed at an angle p, preferably about 36 degrees. The flat portion 1281 is preferably a tangent line to both the curved summit 1279 and the curved trough 1205. Preferably, the length of the leading portion 1275, from the bottom of the curved trough 1205 to the top of the curved summit 1279 is about 0.5 mm. The trailing portion 1277 of peaks 1203 does not include a flat portion. Instead, in the trailing portion 1277, the curved summit 1279 and the curved trough 1205 are tangent to one another.

As shown in FIG. 2A, in accordance with another aspect, a chamfered surface 1018 having an angle q provides a transition surface at the junction of the outer perimeter of annular wall 1051 and the gripping features 1201, 1251 of upper and lower vertebral engaging surfaces 1019, 1021 to further reduce stress concentration. As shown in FIG. 2B, in another form, an additional chamfered surface 1058, also having the angle q, provides a transition surface at the junction of the inner perimeter of annular wall 1051 and the gripping features 1201, 1251 of upper and lower vertebral engaging surfaces 1019, 1021. In one preferred form, the angle q is about 45 degrees.

As a result of the configuration of the implant body 1001 and the preferred materials from which it is formed, the implant body 1001 will more quickly fuse to the adjacent vertebral bone than conventional implant bodies and thereby reduces the risk of slippage or expulsion over time.

The surfaces of the implant body 1001 can be polished to further reduce stress concentration such as by rounding any sharp edges. The polishing or buffing process also provides the medical benefit of preventing contamination within any surface defects, i.e. pits, nicks, or scratches. The polishing process may involve applying abrasives to the implant body 1001 at high speed to remove any surface defects. In addition, tumble polishing can be used to polish the implant 1001 to reduce surface defects.

As noted above, the implant body 1001 preferably does not include any holes, channels, penetrations and the like that are not aligned with the direction of compressive force applied to the implant body 1001 when implanted in the intervertebral space (i.e., along the axis 1001A). For example, to minimize any weakening of the posterior wall portion 1003 and anterior wall portion 1005, and to eliminate any sources of stress concentration, the implant body 1001 preferably includes only throughbore 1009 extending along axis 1001A. Annular wall 1051 is preferably smooth and continuous, without any openings, apertures, channels, or other three-dimensional texture therein.

In conventional VBRs, holes, penetrations, channels, and the like are often present to allow for attachment points for insertion tools, radiographic markers, or through openings for blood flow. For example, prior art implant 7001, shown in FIG. 14, contains numerous holes and penetrations, including an attachment point 7301 for providing a secure connection between the prior art implant 7001 and an insertion tool (not shown), opening for radiographic markers 7303 for allowing a clear view of the orientation and position of the prior art implant 7001 during x-ray examination, and through openings 7305 to encourage and promote bone ingrowth.

As can be seen, for example, in FIGS. 1, 2A and 2B, the implant body 1001 is formed as a solid ring-like structure surrounding throughbore 1009. However, the implant body 1001 and the tools and procedures for implanting the implant body 1001 are advantageously configured to provide the various benefits of the holes, channels and penetrations discussed above with respect to the prior art implant. For example, implant body 1001 includes no attachment points, such as attachment point 7301, and instead, includes a smooth, generally flat surface of anterior wall portion 1005 that cooperates with and provides an intimate engagement with a complementary engagement portion of an insertion tool (such as insertion tool 6001 shown in FIGS. 10-19 and discussed in detail subsequently). As shown, the implant body 1001 does not include any radiographic markers, such as radiographic markers 7303, but instead, is formed of a dense, radio-opaque material such as a nanocrystalline HA or TCP material, which allows the location of the implant body 1001 to be readily seen on X-ray. The necessity of through openings, such as through openings 7305, is avoided by configuring the implant body 1001 to provide maximized void area (i.e., with void or throughbore 1009) and an optimized ratio of void radius to wall thickness to allow bone growth therethrough and blood circulation from blood vessels within the vertebrae themselves.

The implant devices in accordance with the present invention can be made from any suitable, structurally strong, biocompatible material (i.e., nonreactive and non-antigenic to biological systems), which is compatible with the uses and environments into which the implant devices will be utilized. The advantage of using synthetic bone implants includes its ability to provide strong, biocompatible, and resorbable clinical performance.

Preferably, an implant body in accordance with the present invention is formed of hydroxyapatite (hereinafter "apatite" or "HA"), tricalcium phosphate ("TCP") or similar bone substitutes (i.e. synthetic bone) capable of being absorbed into the body and replaced with solid living bone.

More preferably, an implant body in accordance with the present invention is made from a nanocrystalline HA and/or TCP, such as described in U.S. Pat. No. RE 39,196 and U.S. Patent Application Publication No 2005/0031704, respectively, which are hereby incorporated herein in their entirety. These preferred materials are very dense, having a very small crystal size, which allows formation of an implant having superior structural performance, greater reliability, and better mechanical properties compared to implants formed of conventional HA or TCP materials.

The preferred nanocrystalline HA possesses greater reliability, better mechanical properties, and enhanced bioactivity compared to conventional HA with a micron scale microstructure. With minimized flaw sizes, the preferred HA compositions are densified without additives at substantially lower temperatures and demonstrate unusual strength and ductility compared to the conventional polycrystalline HA. Nanostructured HA not only provides superior mechanical properties, but also offers the potential for superplastic net-shape forming for inexpensive rapid prototyping. Additionally, preferred HA can be structurally reinforced by nanocomposite processing involving incorporation of species such as zirconia.

HA compositions preferred for use in the present invention are preferably nanocrystalline. Crystal size typically governs bulk properties in an article, with smaller crystal sizes being advantageous for purposes of the invention. Minimization of particle size, by minimizing crystal size, makes densification of particles easier because smaller particles can re-arrange and pack more readily and have a greater driving force for densification. Accordingly, preferred nanocrystalline apatite powders for use in the present invention have an average particle size that approaches the average crystal size of the material.

A wet chemical approach is used to prepare such preferred materials, in which nanocrystals are precipitated, followed by recovery of powder in which the crystals (which define individual particles) are agglomerated to a minimal extent. Further processing involves densification of the powder into a composite article. The method of forming the preferred nanocrystalline materials is applicable to a wide variety of materials, such as fluoroapatites, hydroxyapatite and carbonate apatite (Type A and Type B) represented by the general formula $M_{10}^{2+}(ZO_y^{3-})_6X^{2-}$, where M=Ca, Ba, Sr, Mg, Pb, Cd, etc. where M can be substituted with Na and/or K and consequently the formula can be substituted with an appropriate number of vacancies and/or anions, as known by one of ordinary skill in the art; $ZO_y=PO_4$, $AsO_4$, $VO_4$, etc. where $ZO_y$ can be substituted with $SiO_4$, $SO_4$, $CO_3$, $BO_3$, etc. to balance a total charge of cations, as known by one of ordinary skill in the art; and $X=F_2$, $(OH)_2$, $Cl_2$, $Br_2$, $I_2$, O, $CO_3$ etc. A preferred set of compounds are those that form hexagonally-packed crystals. Calcium-based apatites such as hydroxyapatite are particularly preferred.

Such bioceramic compositions are easily formable without expensive machining because of their small crystal and particle size. Because of the small particle size of the compositions preferred for use in the invention, sintering can take place at low temperatures, eliminating or minimizing decomposition. The compositions can be sintered to a high theoretical density without "sintering aids" which are known, such as glasses and glassy oxides. They can be densified without external pressure at low temperature for short periods of time, for example no more than 2 hours, preferably no more than 1 hour, and more preferably no more than 30 minutes.

Such compositions can also advantageously be used to make relatively porous material for use in high-surface-area, flowable materials such as cement. In some cases, porosity can be tailored for a particular purpose such as for bone ingrowth where pores of approximately 200 microns may be desirable.

The preferred nanocrystalline HA material, having very small crystal sizes, makes it ideal for powders or coatings, and for use with bones. The crystal size of healthy bone is approximately 20-30 nm, and material having similar crystal size will be better compatible with bone as a result. In particular, the preferred nanocrystalline HA provides has an average crystal size of less than 250 nm according to preferred embodiments. Preferably, the crystal size is less than 150 nm, more preferably less than 100 nm, more preferably less than 50 nm. In accordance with another aspect, the preferred nanocrystalline HA material has a small average particle size, in particular an average particle size of less than 1 μm, preferably having an average particle size of less than 0.5 μm, more preferably still an average particle size of less than 0.25 μm. Any combination of preferred particle size and preferred crystal size can define a preferable combination for use in the present invention, for example an average crystal size of less than 150 nm and an average particle size of less than 1 μm, etc.

A loosely agglomerated nanocrystalline HA powder preferred for use in the invention is obtained by carefully controlling processing parameters affecting the molecular and structural development of HA such as precursor type, precursor concentration, addition rate of precursors, aging time, reaction and aging temperature, and pH during synthesis, as well as by controlling parameters affecting the agglomeration of ceramic particles such as washing and drying of the as-synthesized gel. By minimizing particle size, packing and densification is enhanced, resulting in the fabrication of densified nanocrystalline HA by using a simple pressureless sintering process at relatively low sintering temperatures. By reducing crystallite sizes, ceramics become more ductile as the volume fraction of grain boundaries increases allowing grain boundary sliding. Nanostructured HA also allows superplastic net-shaped forming for inexpensive production. Furthermore, by achieving smaller crystallite sizes, defect size is reduced. With minimized flaw sizes, nanocrystalline HA may be densified with minimal or no sintering additives at substantially lower temperatures and demonstrates improved strength compared to the conventional polycrystalline HA. Thus, preferred nanocrystalline HA possesses greater reliability and better mechanical properties compared to conventional HA with a coarser microstructure. Additionally, the preferred HA can be structurally reinforced by nanocomposite processing such as incorporating nanocrystalline zircona into HA. Additionally, carbonate ions be substituted for phosphate ions in HA to yield carbonate apatite, both Type A and Type B.

The preferred compositions for use in the invention are particulate ceramics, preferably HA, that have high surface area. In one form, the surface area is at least 40 $m^2$/g, preferably at least 60 $m^2$/g, more preferably at least 100 $m^2$/g, more preferably still at least 150 $m^2$/g. The composition is particularly robust and resistant to phase decomposition.

Preferred nanocrystalline HA compositions for use in the invention, alone or as part of a composite including an auxiliary structural additive, preferably undergo apatite phase decomposition of less than 10% when exposed to conditions of at least 100° C. for at least 2 hours. More preferably, the composition undergoes apatite phase decomposition of less than 5%, and more preferably less than 3% under these conditions. In another form, the preferred composition undergoes apatite phase decomposition of less than 10% when exposed to conditions of at least 1100° C. for at least 2 hours, preferably less than 5% and more preferably less than 3% under these conditions. In yet another form, apatite phase decomposition of less than 10% is realized when the composition is exposed to conditions of at least 120° C. for at least 2 hours, and apatite phase decomposition is preferably less than 5% and more preferably less than 3% under these conditions. In yet another form, once exposed to conditions of at least 1300° C. for at least 2 hours, such compositions undergo apatite phase decomposition of less than 10%, preferably less than 5%, and more preferably less than 3%.

The implant device of the present invention is preferably formed of a densified nanocrystalline apatite article where "densified" is defined as having undergone a densification step to create a self-supporting particle and, preferably, densified to a theoretical density of at least 75%, preferably at least 90%, more preferably at least 95%, and more preferably still at least 98%. Porous articles can be provided in accordance with the invention, for example for stimulating bone ingrowth. Where porosity is desired, articles having a porosity of at least 20% are preferred, more preferably at least 30%, more preferably at least 50%, and more preferably still at least 75%.

As used herein, "densified" can be defined in terms of the compressive strength of the article, with densified articles of the invention preferably having a compressive strength of at least about 150 MPa, more preferably at least about 500 MPa, and more preferably still, at least about 700 MPa.

The preferred nanocrystalline compositions can be provided as consolidated particulate apatite, where "consolidated" is meant to define a collection of apatite particles that forms a self-supporting structure. Apatite can be consolidated by providing particulate apatite in a press and compressing the apatite to form an article. The consolidated particulate apatite can be dense or porous.

In one form, a method of forming the preferred nanocrystalline HA compositions involves precipitating apatite from a solvent by adding a calcium salt to a phosphate source. A preferred calcium source is $CaNO_3$, and a preferred phosphate source is $[NH_4]_2PO_4$. However, suitable calcium salts and phosphate sources would be readily recognized by those of ordinary skill in the art. In one form apatite is precipitated from a solvent containing a calcium salt in a concentration of less than 1 M, preferably less than 0.5 M, and more preferably from about 0.16 M to about 2.1 M. Preferred methods include precipitating apatite from a solvent containing a calcium salt and phosphate source in a molar ratio of about 10:6. In another form, a calcium source and a phosphate source in any suitable way.

Preferred rates of addition of calcium source to phosphate source are less than about 0.010 mols calcium source per minute, preferably less than about 0.007 mols/minute, more preferably still less than about 0.005 mols/minute.

The apatite is preferably precipitated from a solvent at a pH of about 7 to about 14, more preferably about 11 to about 13. Apatite crystals are precipitated having a crystal size according to preferred embodiments described above, and precipitated particulate apatite having surface areas as described above, in particular preferably at least 40 $m^2$/g, 60 $m^2$/g more preferably at least 100 $m^2$/g, and more preferably still at least 150 $m^2$/g, are recovered. It has also been found that wet grinding the resulting precipitate from the precipitation step of the invention is advantageous.

The precipitated apatite product is preferably aged at a temperature of between about −25° C. and above 100° C., more preferably between about 10° C. and about 50° C., and more preferably still approximately room temperature, i.e. about 20° C. The apatite is preferably aged for at least one minute.

In another form, the nanocrystalline apatite is calcined under a set of conditions that allow recovery of apatite product that is particularly pure and robust as described above. Preferably, the recovered apatite product is of a nature such that it can be sintered at mild conditions of temperature less than 1100° C., yet results in a product having a theoretical density of at least 95% and a grain size of less than 225 nanometers. Most preferred are products which can be sintered at a temperature of less than 1000° C. resulting in a product having a theoretical density of at least 98%, and a nanostructured apatite product recovered preferably has a BET surface area of at least 40 $m^2$/g and a crystal size of less than 250 nm.

A preferred sintering technique results in very low decomposition. Pressureless sintering preferably takes place at a temperature of no more than 1100° C. for a period of time of no more than 2 hours, more preferably no more than 1000° C. for this period of time, and more preferably still no more than 900° C. for 2 hours. Apatite phase decomposition of less than 10% occurs in this sintering step, preferably decomposition of less than 5%, preferably less than 3%. Sintering can be carried out in the absence of sintering aids. Such additives are known, and are mentioned above. Pressureless sintering is preferred and is possible because of the nature of the bioceramic compositions. In particular, the average crystal size of particulate apatite preferred for use in the invention is small enough that the composition can be sintered to a theoretical density of at least 90% by pressureless sintering, preferably at least 95%, and more preferably still, at least 98% by pressureless sintering, in each case, at a grain size preferably of less than 225 nanometers, at a temperature of no more than 1200° C. in one set of embodiments, more preferably no more than 1100° C., more preferably no more than 1000° C., and more preferably still, no more than 900° C. The pressureless sintering steps can be carried out to result in a densified apatite product having undergone decomposition of less than 10%, more preferably less than 5% and more preferably still less than 3%.

According to another aspect, techniques for colloidal and hot pressing of apatites are utilized to prepare preferred nanocrystalline HA materials. Hot pressing is a form of pressure-assisted sintering whereby a pressure is applied uniaxially to a powder contained within the die during sintering under a vacuum. The pressure-assisted sintering allows for more rapid densification and a lower sintering temperature. However, because the hot pressing occurs under a vacuum, the decomposition reaction of HA is favored, necessitating a lower sintering temperature to prevent decomposition. Colloidal pressing (wet pressing) is a process by which a stabilized sol of HA is uniaxially pressed in a die. A stabilized sol of material is defined as suspension of particles which do not undergo sedimentation appreciably over time. Frits within the dies allow the solvent to escape as the die is pressurized while trapping the solid particles. Once enough solvent is removed to obtain a solid pellet, the pellet is removed and is carefully dried to prevent drying stresses from cracking the pellet. After fully drying the pellet, the pellet is CIPed and undergoes normal pressureless sintering. By avoiding a dry powder plate, colloidal pressing prevents the agglomeration associated with working with a dry powder and benefits from the lubrication effects of the solvent during pressing, which allow the particles in solution to rearrange into the densest packing.

As noted above, according to yet another aspect of the invention, the implant device may be formed of a nanostructured TCP. Resorbable bioceramics, including tricalcium phosphate (TCP), calcium sulfate, and other calcium phosphate salt-based bioceramics, have been used to replace damaged tissue and are eventually resorbed such that host tissue replaces the implant. Problems long associated with resorbable bioceramics are the maintenance of strength, stability of the interface, and matching of the resorption rate to the regeneration rate of the host tissue. Furthermore, the constituents of resorbable biomaterials desirably are metabolically acceptable, since large quantities of material must be digested by cells. This imposes a severe limitation on these compositions. Calcium sulfate typically is used as a rapidly degrading bone filler in cases where mechanical strength is not necessary. Alpha-TCP (alpha-$Ca_3(PO_4)_2$, JC-PDS 9-348) and beta-TCP (beta-$Ca_3(PO_4)_2$, JC-PDS 9-169) typically are used when a rapidly degrading bone filler having more mechanical strength than calcium sulfate ($CaSO_4$, JC-PDS 6-0046) is needed. Though calcium sulfate and TCP degrade rapidly, they both suffer from poor mechanical properties that have limited their applications to bone fillers.

Because calcium phosphate biomaterials are intrinsically bioactive and resorbable, they can be tailored for mechanical strength, resorption and bonding with the surrounding tissue through nanostructure. While alpha- and beta-TCP are widely used and while a TCP formulation having mechanical and morphological properties advantageous for prostheses would be very useful, attempts to date have failed to produce reliable structural TCP implants.

Nanocrystalline TCP (i.e., alpha- and/or beta-TCP) preferred for use with the present invention can be formed into high surface area powders, coatings, porous bodies, and dense articles by a wet chemical approach. This wet chemical approach is preferred because it is versatile, simple, and easy to control, in terms of both the preparative reactions and the characteristics of the reaction product, such as morphology, size, and reactivity. Precursor type, precursor concentration, solvent environment, addition rate of precursors, aging time, aging temperature, and pH during precipitation have been identified as the processing parameters controlling the molecular and structural development of TCP precursor materials. Furthermore, by controlling dry particle formation from the precipitate through washing, drying and comminution, an ultrafine particulate TCP precursor powder can be obtained.

This TCP precursor powder is then transformed into TCP, for example by a calcination step. The calcination temperature can be significantly reduced with the appropriate precipitation conditions permitting the formation of an ultrafine particulate TCP that can enhance packing and densification and lower sintering temperatures. The phase (i.e., alpha or beta) of TCP that is obtained is dependent at least in part on the precipitation and processing conditions and calcinations temperature and environment. Alternatively, a method using microwaves, X-rays, lasers, electron beams or neutron beams can be used to transform precursor powder into TCP.

Dense TCP articles can be fabricated by pressureless or pressure-assisted sintering processes using this ultrafine TCP powder. By reducing the crystal size within an article, the smallest possible defect size is reduced thereby increasing the highest possible strength. In addition, ceramics become more ductile at lower temperatures as the volume fraction of grain boundaries increases allowing grain boundary sliding allowing for rapid superplastic net-shape forming. Furthermore, the resorption profile of dense TCP can be controlled by extending the heat treatment during sintering or through post-sinter thermal cycles to alter the microstructure. The subsequent controlled grain growth can then be used to increase or decrease the resorption rate.

Thus, nanostructured TCP preferred for use in the invention possesses greater reliability and better mechanical properties as compared to conventional TCP having a coarser microstructure. In addition, the preferred TCP can be structurally reinforced by incorporating a secondary reinforcing species into the TCP precursor material during nanocomposite processing.

Preferred particulate TCP for use in the invention preferably has an average TCP crystal size of about 250 nm or less and an average particle size of about 5 µm or less. In another form, the TCP compositions have a BET surface area of about 20 $m^2/g$ or greater.

In another aspect, an implant device of the present invention comprises a consolidated TCP structure having an average crystal size of about 80 µm or less and a density of about 90% of the theoretical density. In yet another form, an implant device of the present invention comprises a consolidated TCP structure having an average crystal size of about 1 µm or less and a porosity of about 20% or greater.

A method of forming the preferred TCP compositions for use in the invention involves calcining a TCP precursor precipitate at a temperature of about 400° C. to about 1400° C. and recovering a nanostructured TCP article having a BET surface area of about 20 $m^2/g$ or greater, a crystal size of about 250 nm or less, and an average particle size of about 5 micron or less.

In another aspect, a preferred particulate TCP composition for use in the invention has an average crystal size small enough that the composition can be sintered to a theoretical density of about 90% or greater by pressureless sintering. In another aspect, a method of forming a preferred TCP composition comprises sintering a composition comprising a TCP to a theoretical density of about 90% or greater by pressure-assisted sintering in the absence of any sintering additives.

Preferred particulate TCP for use in the invention preferably has an average crystal size of about 250 nm or less, more preferably about 150 nm or less, more preferably about 100 nm or less, and most preferably about 30 nm or less (e.g., about 20 nm or less). Alternatively, in some embodiments, it is desirable that the particulate TCP have an average crystal size of about 500 nm or more (e.g., about 1 micron or more, about 3 micron or more, about 12 micron or more, or even about 60 micron or more) in order to retard the rate of TCP resorption.

Typically, the preferred particulate TCP has a narrow log normal particle size distribution. For example, typically about 25% or more of the TCP particles have a particle size of about 1 micron or less. Furthermore, typically 90% or more of the TCP particles have a particle size of about 10 microns or less.

The TCP compositions preferred for use in the present invention may comprise TCP particles having a high surface area. Typically, the BET surface area is about 20 $m^2/g$ or greater, preferably, about 40 $m^2/g$ or greater, more preferably about 100 $m^2/g$ or greater.

The TCP particles can have any suitable morphology, for example the particles can have an aspect ratio of about 1:1 to about 50:1. The morphology of the TCP particles will depend on the desired application. When the TCP particles are to be used to form a densified article, such as an implant device of the present invention, preferably the TCP composition comprises TCP particles that are substantially equiaxed (e.g., having an aspect ratio of about 3:1 or less, about 1.5:1 or less, or about 1:1). When the TCP particles are to be used to form a porous consolidated article or as the reinforcing agent of a dense composite article, preferably the TCP composition comprises TCP particles that are whisker-like (e.g., having an aspect ratio of about 3:1 or more, 5:1 or more, or even 10:1 or more).

Preferably, the TCP precursor material is precipitated from calcium source solutions and phosphate source solutions having a molar ratio of calcium to phosphorous of about 1 to about 2 (e.g., about 1.2 to about 1.8). More preferably, the molar ratio of calcium source to phosphorus source is about 1.4 to about 1.6, more preferably about 1.5 (i.e., 3:2). The TCP precursor material can be formed by addition of a calcium source solution to a phosphate solution, by addition of a phosphate source solution to a calcium source solution, or by simultaneous mixing of a calcium salt solution and a phosphate source solution. Preferably, the calcium salt solution is added to the phosphate source solution.

Control of the mixing rates (e.g., addition rates) of the calcium source to the phosphate source (or alternatively the phosphate source to the calcium source) is advantageous for controlling the size of the resulting TCP precursor crystallites. Desirably, the addition rate of the calcium source to the phosphate source (or vice versa) is about 0.1 mmol/min or more (e.g., about 1 mmol/min or more, about 10 mmol/min or more, about 50 mmol/min or more, or even about 100 mmol/min or more). Preferably, the mixing rate is very large (e.g., instantaneous mixing is most preferred); however, the actual mixing rate typically is limited by the mixing/agitation equipment being used and generally is about 1 mol/min or less (e.g., about 0.8 mol/min or less, or about 0.6 mol/min or less). Preferably, the mixing rate (e.g., addition rate) is about 1 mmol/min to about 1000 mmol/min, more preferably about 10 mmol/min to about 500 mmol/min.

The pH of the calcium and phosphate solutions has been found to be an important parameter for controlling the type of TCP precursor material that is formed. Desirably, the TCP precursor material is precipitated from a solution having a pH of about 5 to about 11, more preferably from about 7 to about 10. When the solution pH is about 5 or 6, the TCP precursor material typically comprises monetite, brushite, or a combination thereof. When the solution pH is 10 or above, the TCP precursor material typically comprises a poorly crystalline apatitic calcium phosphate material. When the solution pH is about 7 to about 10, the TCP precursor material typically comprises predominantly amorphous calcium phosphate, octacalcium phosphate ($Ca_8H_2(PO_4)_6 \cdot 5H_2O$), apatitic TCP, or a combination thereof. The pH of the precursor solutions can be adjusted by addition of one or more common pH adjustors. The pH adjustor can be any suitable pH adjustor, for example nitric acid, acetic acid, ammonium hydroxide, or tetramethylammonium hydroxide (e.g. tetraethylammonium hydroxide or tetrabutylammonium hydroxide). Preferably, the pH adjustor is nitric acid, ammonium hydroxide, or a combination thereof.

The precipitated TCP precursor material is then recovered from the reaction mixture, for example by filtering, filter pressing, centrifugation, or settling and decantation. Preferably, the TCP precursor material is aged prior to recovery. The TCP precursor material can be aged at any suitable temperature and for any suitable amount of time. Typically, the TCP precursor material is aged at a temperature between about 0° C. and about 90° C., preferably between about 5° C. and about 50° C., and more preferably between about 10° C. and about 30° C. Typically, the TCP precursor material is aged for about 1 minute or more (e.g., about 30 minutes or more, or about 60 minutes or more). Preferably, the TCP precursor material is aged for about 2 hours or more (e.g., about 5 hours or more, about 10 hours or more, about 30 hours or more, about 50 hours or more, or even about 100 hours or more). After aging, the TCP precursor material can be collected and then redispersed in a solution having the same solvent and pH as the reaction solution.

The recovered TCP precursor material desirably is dried to form a powder and then is milled. The dry TCP precursor powder can be milled by any suitable method and in the absence or presence of any suitable solvent. Preferably, the dry TCP precursor powder is milled in the presence of anhydrous alcohol, acetone, toluene, or a combination thereof. After milling, the dry TCP precursor powder is dried again.

The preferred TCP compositions may be provided as consolidated particulate TCP, where "consolidated" is meant to define a collection of TCP particles that forms a self-supporting structure. The preferred TCP can be consolidated by any suitable technique, for example by providing particulate TCP in a press and compressing the TCP to form an article. The consolidated particulate TCP can be dense or porous. It has generally been relatively straightforward to make porous ceramic articles, but significantly more difficult to make dense ceramic articles. The very small TCP particle size allows formation of very dense articles. Such dense, strong materials are particularly advantageous for use as implants, such as the implant device of the present invention, where strength is required.

Typically, the consolidated TCP article for use in this invention has an average crystal size (e.g., grain size) of about 80 μm or less, preferably, about 10 μm or less. Alternatively, in some embodiments, it is desirable that the consolidated article has an average crystal size of about 100 nm or more (e.g., about 150 nm or more, or about 200 nm or more). The consolidated article preferably has a crystal size distribution of about ±0.75 (e.g., about ±0.5, about ±0.25, or about ±0.1) times the average crystal size.

The theoretical density of consolidated TCP articles for use in the invention preferably is about 25% or greater, more preferably about 40% or greater, and even more preferably about 55% or greater. In a preferred embodiment, a TCP powder is formed into a densified particulate TCP article where "densified" is defined as having undergone a densification step to create a self-supporting article. Preferably, the TCP powder is densified to a theoretical density of about 60% or greater, more preferably about 90% or more.

The preferred densified TCP articles for use in the present invention typically have a compressive strength (ASTM C 1424-99) of about 150 MPa or greater, preferably about 500 MPa or greater. The three-point bending strength (ASTM C1161-94) typically is about 100 MPa or greater, preferably about 300 MPa or greater. Generally, the three-point bending strength is about 700 MPa or less. The preferred densified TCP articles typically have a fracture toughness (ASTM C 1421-01a) of about 0.5 MPa·m$^{1/2}$ or greater (e.g., about 1 MPa·m$^{1/2}$ or greater, or about 1.5 MPa m$^{1/2}$ or greater). Generally, the fracture toughness is about 5 MPa·m$^{1/2}$ or less (e.g., about 4 MPa m$^{1/2}$ or less). Such preferred densified TCP articles can be partially or fully transparent. Preferably, the articles are able to transmit about 50% or more (e.g., about 70% or more, or about 90% or more) light having a wavelength in the range of about 150 nm to about 1,000 nm.

The consolidated porous articles for use in the invention can have a compressive strength (ASTM C1424-99) of about 50 MPa or greater (e.g., about 100 MPa or greater, or about 150 MPa or greater). In addition, the consolidated porous articles can have a three-point bending strength (ASTM C1161-94) of about 20 MPa or greater (e.g., about 40 MPa or greater, or about 60 MPa or greater). Generally, the compressive strength is about 500 MPa or less and the three-point bending strength is about 400 MPa or less. The consolidated porous articles typically have a fracture toughness (ASTM C1421-01a) of about 0.2 MPa·m$^{1/2}$ or greater (e.g., about 0.5 MPa m$^{1/2}$ or greater). Generally, the fracture toughness is about 1 MPa m$^{1/2}$ or less.

Structural additives can be added to the TCP to structurally reinforce the nanocomposite material. The structural additive can be any suitable structural additive. Suitable structural additives include ceramics, metals, alloys, and combinations thereof. Ceramics preferred for use in composites include metal oxides (e.g., alumina, zirconia, and titania), silicon carbides, silicon nitrides, combinations thereof, and other structural ceramics. Metals preferred for use in composites include Mg, Ti, Ta, Nb, Al, Ni, W, Fe, Mo, Co, Zr, Au, Ag, V, alloys thereof, stainless steel, combinations thereof, and other structural metals. Other suitable structural additives include apatite and carbon. The structural additive can have any suitable size or shape. For example, the structural additive can have the shape of particles, rods, whiskers, plates, nanotubes, or fibers. In particular, structural additives having non-spherical aspect ratios are desirable and contribute to great improvements in the fracture toughness and strength. Preferably, the structural additive is selected from the group consisting of nanocrystalline alumina plates, hydroxyapatite whiskers, carbon fibers or nanotubes, silver particles or rods, zirconia particles or rods, and combinations thereof. The structural additive should be selected to strengthen the composite. The secondary, non-TCP structural component can form a major or minor component, with the overall composite having at least 10% TCP, preferably at least 20% TCP, more preferably at least 50% TCP.

In one form, the TCP porous articles described above are infiltrated with a secondary additive such as HA to form a fully dense article. This composite article will have sufficient strength for load-bearing applications. After implantation, the TCP will be substantially resorbed leaving a porous structure of the secondary composition (e.g., HA) into which bone will ingrow. In another form, a consolidated article (e.g., an implant) comprising a TCP precursor material such as HA is converted to a TCP composite article (e.g., a biphasic HA/TCP composite article). The TCP precursor material can be converted by any suitable means. Preferably, the TCP precursor material is converted through the use of a laser light source (e.g., x-ray, UV, electron, or neutron beam) as described above. For example, the surface of a consolidated or densified HA article can be converted to alpha-TCP and/or beta.-TCP. Using a laser beam is particularly advantageous because the laser can convert the TCP precursor material in predictable ways (e.g., in selected areas of an implant). A biphasic HA/TCP article will have the strength and structural stability of HA combined with the resorptive properties of TCP. The amount of TCP formed on the surface of the article will depend on the penetration of the laser into the surface and the length of time for exposure. Typically, the time of exposure is about 1 min to about 20 min (e.g., about 2 min to about 10 min, or about 3 min to about 7 min). Desirably, about 1 μm to about 250 μm (e.g., about 5 μm to about 125 μm) of the HA surface is converted to TCP, which is more readily resorbed than hydroxyapatite.

In accordance with another form, the implant device of the present invention is made of a nanocrystalline calcium phosphate material such as NANOSS™, an engineered synthetic bone platform utilizing nanotechnology. The NANOSS™ materials have received an FDA clearance for the use as bone void filler, making it the first nanotechnology device approved by the FDA. Recent processing inventions now permit the addition of highly porous surface features to structures to provide a scaffold for accelerated tissue attachment and resorption. The porous surface allows the patient's capillaries to grow into the porous surface of the TCP and is generally referred to as osteoconduction. Clinical studies have shown evidence of boney ingrowth, resorption and boney bridging between the HA and adjacent bone.

The nanotechnology allows for the creation of highly dense nanostructure which provides greater strength and higher surface area to volume. The greater surface area to volume allows the cells of the patient to better absorb and integrate the material into the skeletal system because the nanostructure of the NANOSS™ materials allows for more surface contact and is the correct scale in size to allow biological cellular interaction.

NANOSS™ HA is assembled from calcium and phosphate beginning at the molecular level to produce structural products with unique structural and functional properties. NANOSS™ HA is structurally robust calcium phosphate able to be formed into implant devices that provide sufficient strength for use as a vertebral body replacement while providing the implant site a matrix on and through which new bone can grow. This capability is provided by the unique size and chemical structure of the calcium phosphate materials produced using nanotechnology processes as well as the ability to form complex shapes while preserving desirable material characteristics.

Alternatively, a composite composition composed of a combination NANOSS™ HA and NANOSS™ TCP can be formed with other optional reinforcing materials. NANOSS™ HA has superior overall strength with good resorption properties, but has non-ductile ceramic material characteristics. NANOSS™ TCP has superior resorption properties with good durability, but is not as strong as HA. The composite mixture of HA and TCP allows the tailoring and optimization of the material properties to create an implant that balances strength, durability, resorption, and the ability to be machined for large scale production.

A solid NANOSS™HA formed implant allows ingrowth of tissue into the HA to create an eventual fusion between the implant and the adjacent bone. This fusion of the implant and patient provides the solid skeletal structural support desired which is similar to that of living bone. However, in an alternative embodiment, the HA materials can be introduced into the patient in both a solid and viscous form simultaneously thus allowing for the implanted HA device to be cemented into place with viscous HA. In yet another embodiment, the viscous cement form of HA can also be injected into structurally weakened bone of the patient, such as bone weakened by osteoporosis, to reinforce the patient's bone near the implant.

Implant devices of the present invention undergo some special manufacturing processes. In one preferred form, the implant material (preferably a nanocrystalline HA and/or TCP material), is initially manufactured into a dense article having the shape of a short cylinder or puck. The puck is then milled to achieve its final shape, forming peaks and troughs in the upper and lower vertebral engaging surfaces and creating the central throughbore. Any suitable means for cutting and shaping the implants may be used. Diamond tooling is preferred.

Figure 6:
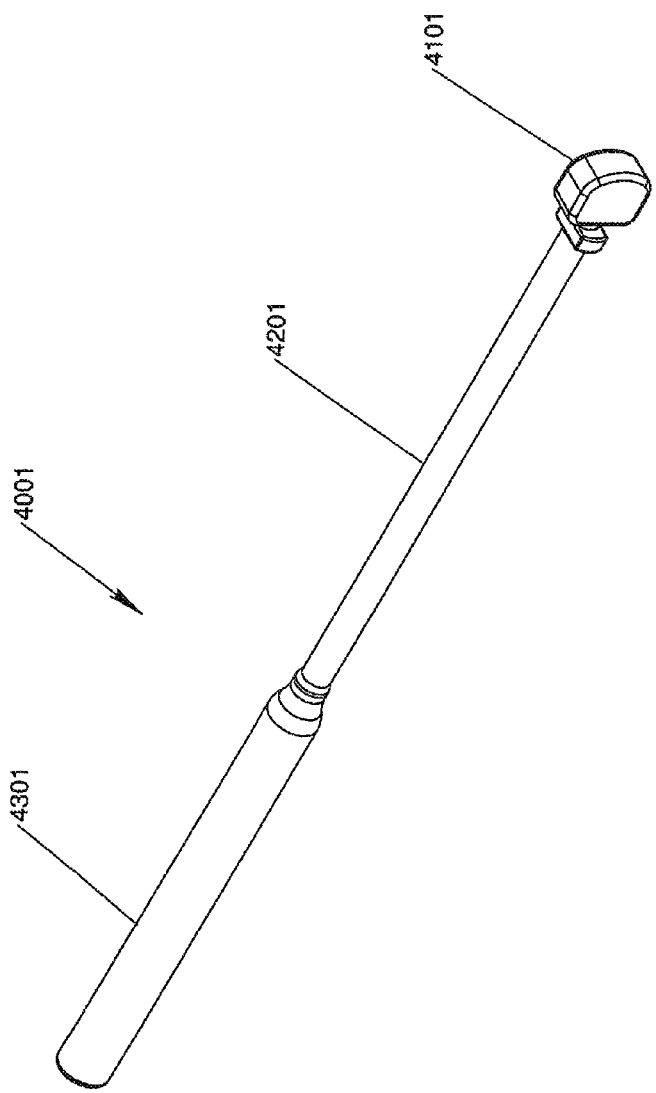
FIG. 6 is a perspective view of a trial spacer tool in accordance with another aspect of the invention.

In accordance with another aspect of the invention, a trial spacer tool 4001 is shown in FIGS. 6, 7A, and 7B. The trial spacer tool 4001 may be used prior to insertion of an implant device of the present invention to determine the relative size of the intervertebral space and verify the existence of sufficient space between the vertebrae for the insertion of an implant. In one embodiment, the trial spacer tool 4001 comprises a handle portion 4301, a shaft portion 4201 extending therefrom, and a generally "D" shaped protuberance or spacer 4101 connected at the distal end of the shaft portion 4201. The "D" shaped spacer 4101 is configured to correspond in size and shape to one of the various size implant bodies 1001 described herein. In one embodiment, the "D" shaped spacer 4101 has a corresponding tapered wedge shape. The spacer 4101 may have a polished surface to allow for ease of insertion of the spacer 4101 into a vertebral space. In one preferred form, the spacer 4101 is made of 17-4 stainless steel, however, any suitable material may be used.

The shaft portion 4201 preferably has a cylindrical shape with a distal threaded male connection 4203 for threadably engaging a female threaded connection 4103 of the spacer 4101. The shaft portion 4201 likewise has a proximal threaded male connection 4205 for threadably engaging a corresponding female threaded connection 4303 of the handle portion 4301. The shaft portion 4201 is preferably solid, and may be formed of any suitable material, however, 17-4 stainless steel is preferred.

The handle portion 4301 may include a knurled or textured surface to improve the grip of the operator.

Figure 8:
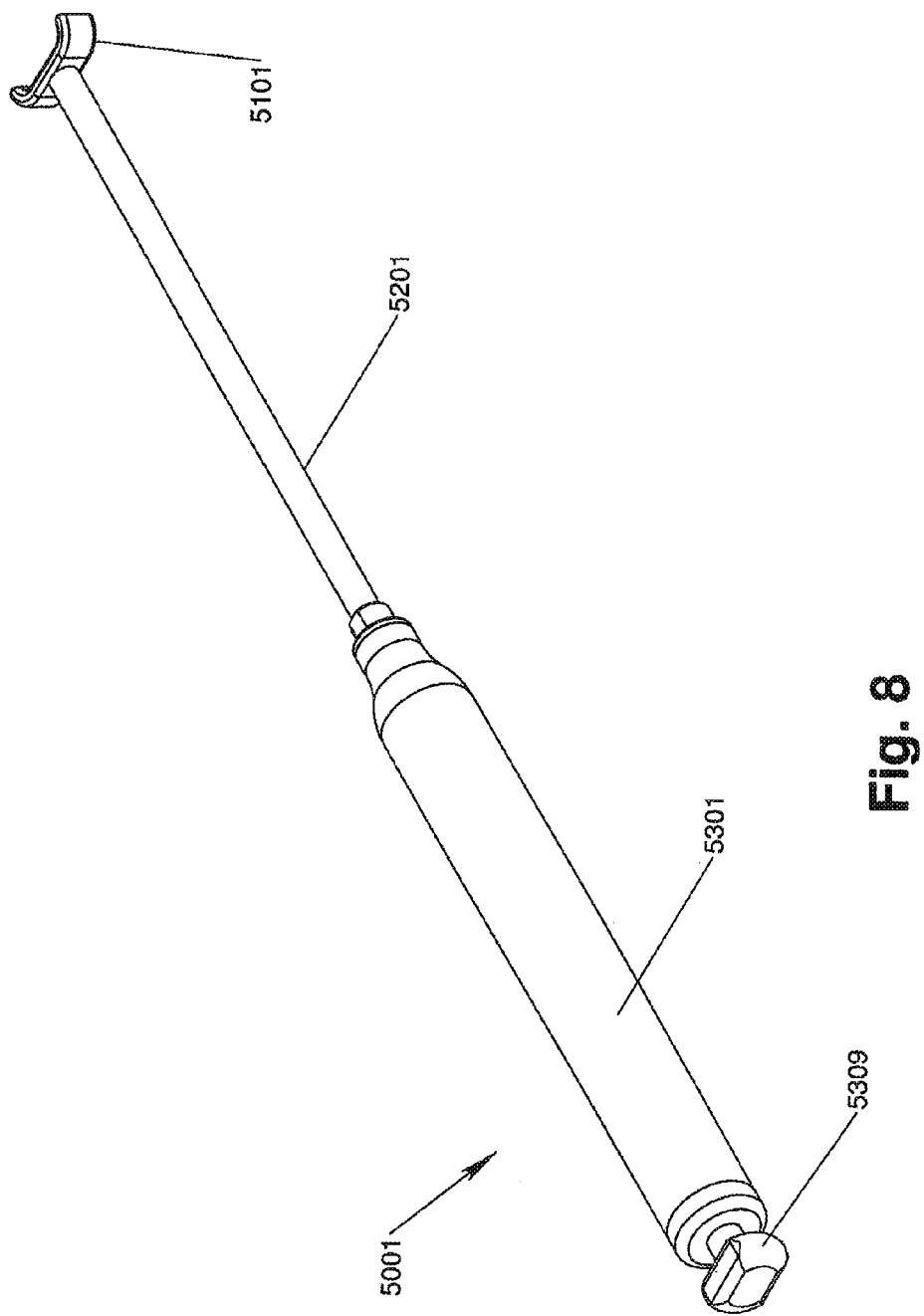
FIG. 8 is a perspective view of tamp device in accordance with another aspect of the invention.
Figure 10:
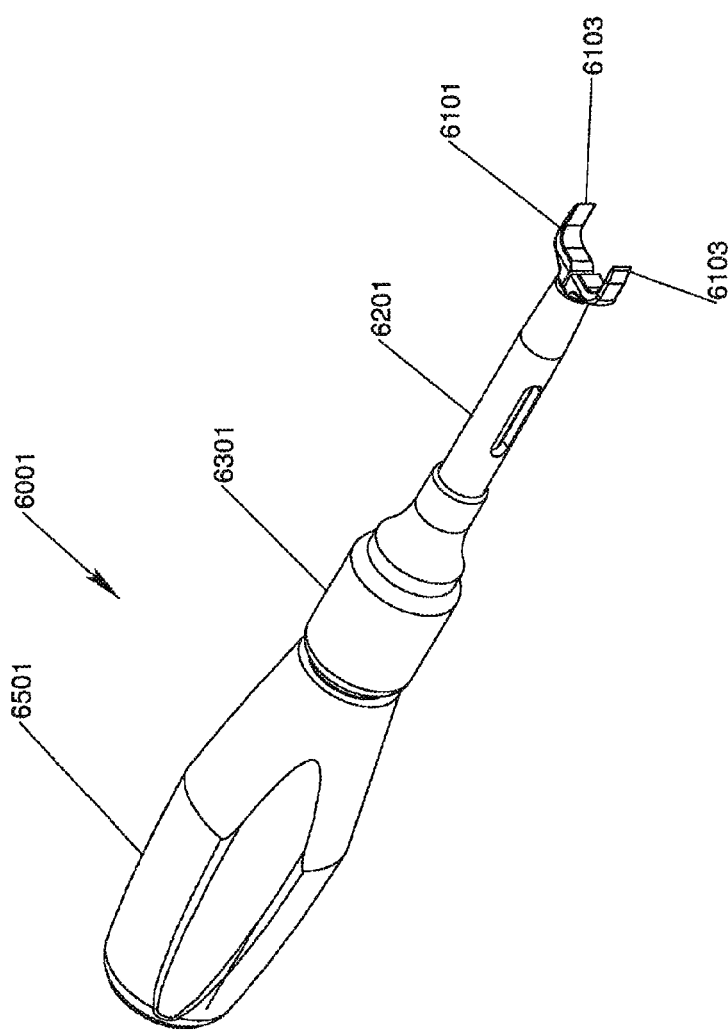
FIG. 10 is a perspective view of an implant insertion tool in accordance with another aspect of the invention.
Figure 11:
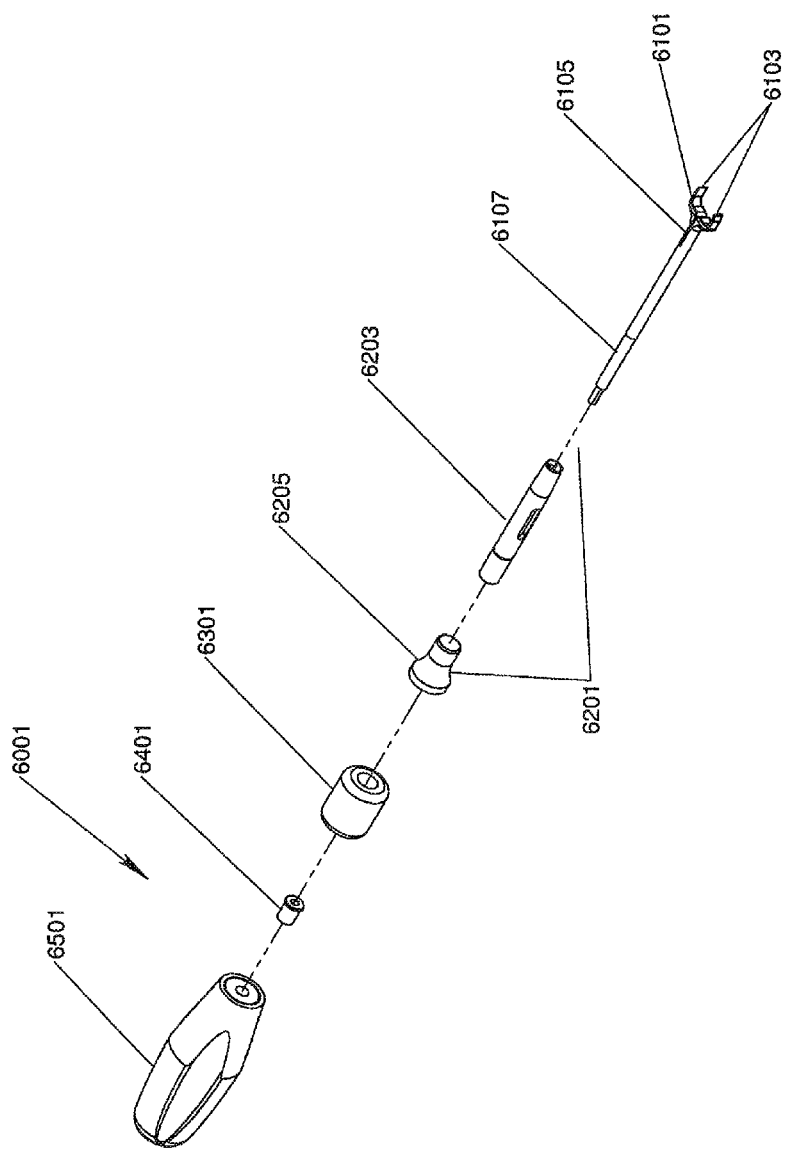
FIG. 11 is an exploded view of the implant insertion tool of FIG. 10.
Figure 13:
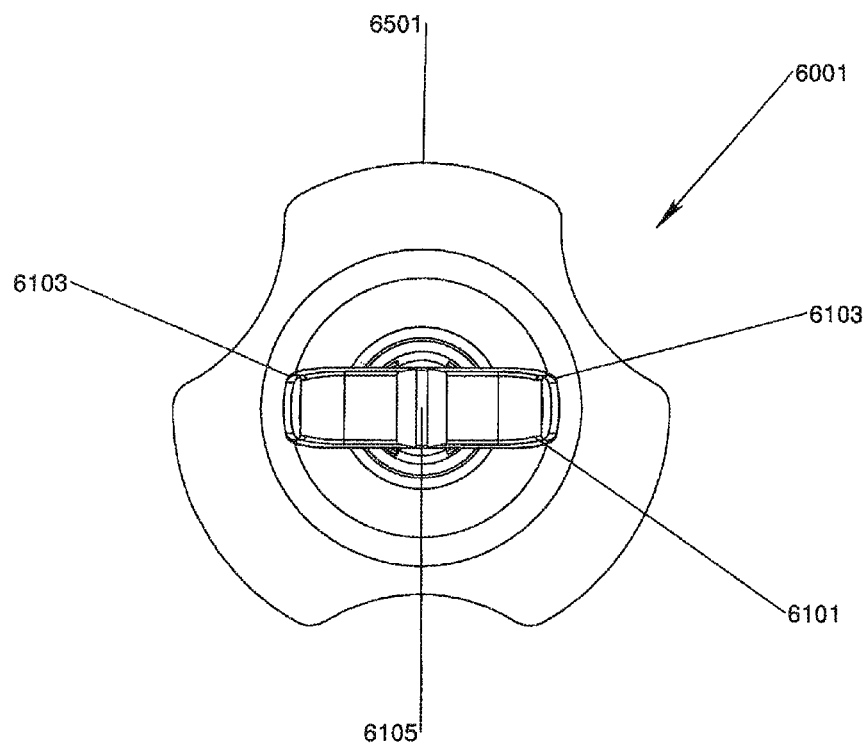
FIG. 13 is a front view of the distal end of the implant insertion tool of FIG. 10.

In accordance with yet another aspect of the invention, a tamp device 5001 is shown in FIGS. 8, 9A and 9B. Tamp device 5001 may be used to assist the surgeon in achieving proper placement of the implant. In one embodiment, the tamp device 5001 comprises a handle portion 5301, a shaft portion 5201 extending therefrom, and a protuberance 5101 connected at a distal end thereof.

The protuberance 5101 may be configured to correspond in shape and size to a portion of the implant body 1001. In one form, the protuberance 5101 has a generally crescent shape, preferably, with a width 5105, conforming to the anterior wall portion 1005 of the implant body 1001. In another form, the protuberance 5101 can have the same general shape as shown in FIG. 8 but with thinned edges of the distal end to allow increase access into the vertebral space. In another form, the protuberance 5101 may be a solid box for extremely tight vertebral spaces.

The protuberance 5101 is preferably threadably connected to the shaft portion 5201 via a female threaded connection 5103 of the protuberance 5101 and a male threaded connection 5203 at the distal end of the shaft portion 5201. Likewise, the handle portion 5301 is preferably threadably connected to the shaft portion 5201 via a female threaded connection 5303 of the handle portion 5301 and a male threaded connection 5205 at the proximal end of the shaft portion 5201. The handle portion 5301 may include a knurled or textured surface to improve the grip for the operator. The handle portion 5301 may also include a slap-hammer cap 5309 at the proximal end that allows the surgeon to apply impact loads to position the implant device.

The tamp device 5001 may be formed of any suitable material. Preferably, the protuberance 5101 is formed of a biocompatible material, such as PEEK, the shaft portion 5201 is 17-4 stainless steel, and the handle portion 5301 is anodized aluminum.

In accordance with another aspect of the invention, an inserter tool 6001 as shown in FIGS. 10-13, may be used to insert the implant body 1001 into the intervertebral space. The inserter tool 6001 comprises a handle portion 6501, an inner shaft portion 6107 extending therefrom, and an implant engaging tong portion 6101 at the distal end of the inner shaft portion 6107. The inner shaft portion 6107 is received within a central passage of a threaded knob 6301 in communication with an outer shaft assembly 6201.

The implant engaging tong portion 6101 comprises a pair of tong arms 6103 configured to securely grip the implant body 1001 (without the need for any engagment holes, channels or penetrations in the implant body), allow proper implantation of the implant, and mechanically release the implant once in position. A narrow slit 6105 extends along a portion of the inner shaft portion 6107 from the distal end thereof and thereby defines and separates the tong arms 6103 and allow deflection of the tong arms 6103.

The tong portion 6101 is preferably configured to correspond in size and shape to a portion of the implant body 1001. In one embodiment, the tong portion 6101 is generally crescent shaped. In a preferred embodiment, the tong portion 6101 is shaped to conform to the anterior wall portion 1005 of the implant body 1001. The tong portion 6101 has a predetermined width to generally correspond to the width of the anterior wall portion of the implant body 1001. In one form, the tong arms 6103 are preferably made of 17-4 stainless steel and low friction chrome coated, hardened, and electropolished to allow the implant to easily connect and disconnect to the tong arms 6103.

As shown, for example, in FIG. 12B, the inner shaft portion 6107 provides an axis that penetrates and constrains the outer shaft assembly 6201 and the knob 6301. The inserter tool 6001 functions through force exerted on the crescent shaped tongs 6103 when the outer shaft assembly 6201 is driven forward by rotating the knob 6301 clockwise. The outer shaft 6203 mechanically interferes with the tong arms 6103 and forces the tong arms 6103 to deflect inward via a cam action. The deflection of the tong arms 6103 allows a compressive force to be applied by the tong arms 6103 to the implant body 1001 to securely hold the implant and provide an intimate engagement therewith. The implant can be released by removing the driving force by rotating the knob 6301 counter-clockwise.

In one embodiment, the outer shaft assembly 6201 is made up of the outer shaft 6203 and the flange 6205, both of which are preferably made of 17-4 stainless steel. The outer shaft 6203 includes a hollow cylinder that transmits a linear force from the knob 6301 to the tong arms 6103. The outer shaft 6203 is connected via a threaded connection 6207 to the flange 6205. The flange 6205 provides the mechanical link to the knob 6301.

The knob 6301 allows rotational force to be applied by the operator, i.e. the surgeon, to the inserter tool 6001. The surgeon applies rotational force, i.e. a torque, to the knob 6301. Drive threading 6307 between the inner shaft 6107 and the knob 6301 cause the knob 6301 to move in the distal direction in response to the rotational force applied thereto. The movement of the knob 6301 in the distal direction in turn provides a linear force to the outer shaft assembly 6201 which is transmitted distally to the tong arms 6103. The knob is preferably made of 17-4 stainless steel, and may preferably have a knurled or textured surface.

The handle portion 6501 preferably has a textured surface 6503 for the operator to apply a counter-torque to the torque applied to the knob 6301 to keep the tong portion 6101 from rotating within the vertebral space. In one embodiment, the textured surface 6503 is a molded flexible material, such as silicone, that provides finger grooves and texture to assist in providing an ergonomic interface between the inserter tool 6001 and the operator. The textured surface 6503 may also be molded onto an outer handle core 6507 which is also preferably made of silicone. In one embodiment, an outer handle core 6507 forms a female mating surface for receiving a male mating surface 6511 of a cap 6505. The outer handle core 6507, cap 6505, and textured surface 6503 may all be connected by a force fit connection.

The outer handle core 6507 is connected to an inner handle core 6508, preferably of 17-4 stainless steel. The inner handle core 6508 may include female threaded connection 6509 received in a male threaded connection 6405 of a plug 6401. Plug 6401 then connects the handle 6501 to the rest of the inserter tool 6001. Plug 6401 is preferably welded to the inner shaft 6107. In addition, the plug 6401 may be configured to include male threads 6405 for threadably engaging the handle portion 6501. Plug 6401 is preferably made of 17-4 stainless steel.

In accordance with yet another aspect of the invention, an inserter tool 8001, as shown in FIGS. 15-18, may be used to insert the implant body 1001. Like the inserter tool 6001, the inserter tool 8001 operates to gently grasp the implant 1001 without the need of any holes, channels, and/or attachment points in the implant body 1001. Likewise, the inserter tool 8001 comprises a handle portion 8401, an inner shaft portion 8107 extending therefrom, and an implant engaging tong portion 8101 at the distal end of the inner shaft portion 8107. The inner shaft portion 8107 is received within a central passage of a threaded knob 8301 in communication with an outer shaft portion 8201.

The tong portion 8101 is preferably generally crescent shaped to conform to the anterior wall portion of the implant body 1001. As shown, for example, in FIGS. 16 and 17B, tong portion 8101 comprises tong arms 8103 separated by a narrow slit 8105 in the distal end of the inner shaft portion 8107, and bumpers 8109, 8111 received within apertures 8117, 8119 at the distal portion of tong arms 8103.

The bumpers 8109, 8111 are preferably made of PEEK. PEEK is a biocompatible semicrystalline thermoplastic with excellent mechanical and chemical properties. PEEK is elastic yet both tough and highly resistant to thermal degradation in both organic and aqueous environments such as during sterilization. Other suitable materials include, for example, polymers of the poly-aryl-ether-ketone family.

The portions of the bumpers 8109, 8111 that interface with the tong arms 8103 provide a shock absorber between the inserter tool 8001 and the implant body 1001. The bumpers 8109, 8111 advantageously function to absorb or dissipate energy imparted to the inelastic implant body. Reduction of shock load to the implants is particularly advantageous because of the inelastic nature of the nanocrystalline structure of the implants themselves which makes the implants susceptible to shock loading during insertion.

The bumpers 8109, 8111 are preferably secured within apertures 8117, 8119 of tong arms 8103 via pins 8113, 8115. The tong arms 8103 and pins 8113, 8115 are preferably made of stainless steel.

The narrow slit 8105 allows the tong arms 8103 to deflect with respect to one another. As with inserter tool 6001, the inner shaft portion 8107 of inserter tool 8001 provides an axis that penetrates and constrains the outer shaft portion 8201, the knob 8301, and the handle 8401. The proximal end of the inner shaft 8107 is preferably threadably engaged with the handle portion 8401 via threading 8403. The inner shaft 8107 and tong arms 8103 are preferably made of 17-4 stainless steel.

As shown, for example in FIG. 17B, the components of insertion tool 8001 are assembled to allow the tong portion 8101, including bumpers 8109, 8111 to engage and disengage the implant body 1001 via the rotation of the knob 8301. More specifically, the inserter tool 8001 functions through deflection motion on the tong arms 8103 and bumpers 8109, 8111. The outer shaft 8201 is driven forward by rotating the knob 8301 clockwise and thereby mechanically interferes with the tong arms 8103 and forces the attached bumpers 8109, 8111 to deflect inward via a cam action between the outer shaft 8201 and tong arms 8103. The deflection of the tong arms 8103 allows the bumpers 8109, 8111 to intimately engage, and thereby securely hold, the implant body. The implant body can be mechanically released by rotating the knob 8301 counter-clockwise.

In the preferred embodiment, the outer shaft portion 8201 includes a number of apertures 8203 and a flange portion 8205. The apertures 8203 provide connection points for a stop 8501 at the distal end of the inserter tool 8001. The apertures 8203 also function as flow ports to assist in cleaning the inserter tool 8001. The flange portion 8205 provides the bearing surface and mechanical link for the knob 8301.

The knob 8301 allows a rotational force to be applied by the operator to the inserter tool 8001. The rotational force causes the knob 8301 to move in the distal direction because of drive threading 8307 between the inner shaft portion 8107 and the knob 8301. The movement of the knob 8301 in the distal direction in turn provides a linear force to the outer shaft portion 8201, which is transmitted distally to the tong arms 8103. The knob 8301 is preferably made of 17-4 stainless steel. The knob may include a knurled or textured surface 8303, which provides a gripping surface for the operator.

The handle portion 8401 also preferably provides a knurled or textured grip 8404 for the operator to apply a counter-torque to the torque applied to the knob 8301 to keep the tong portion 8101 and bumpers 8109, 8111 from rotating within the intervertebral space.

A cap 8405 is threadably connected to the handle portion 8401 via threading 8407. Both the cap 8405 and handle 8401 are preferably made of 17-4 stainless steel.

Figure 19:
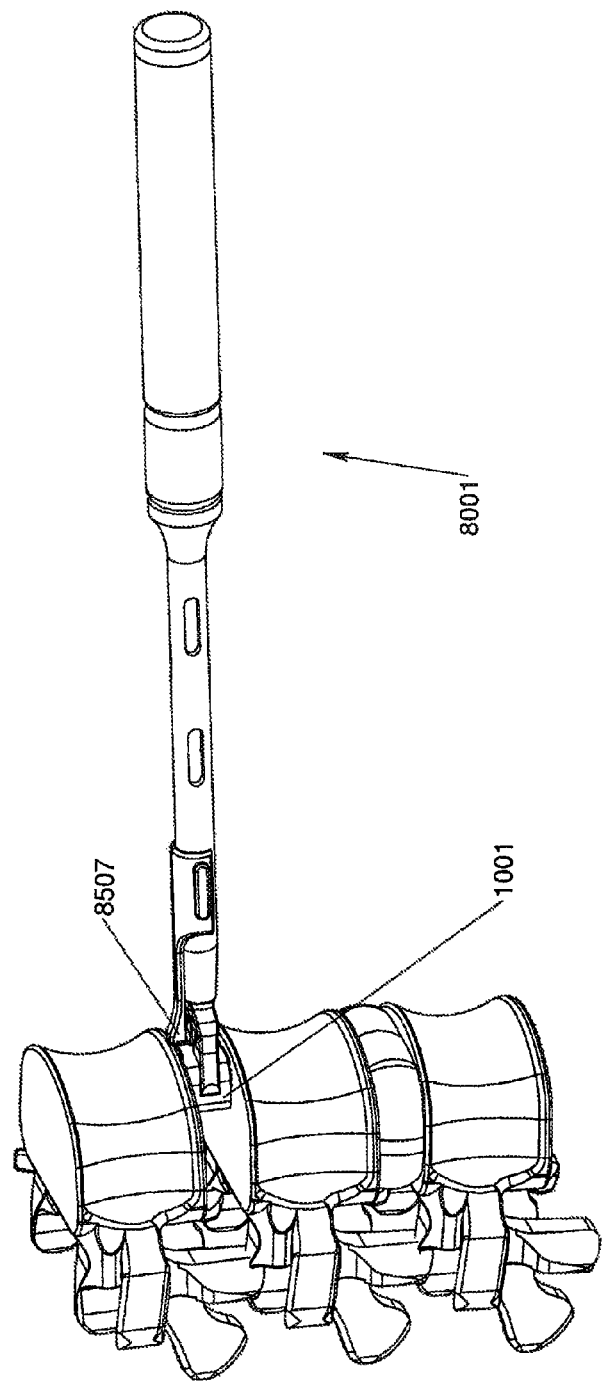
FIG. 19 is a perspective view of a portion of a spine showing the implant insertion tool of FIG. 15 inserting an implant device of FIG. 1 into the intervertebral space.

Inserter tool 8001 also preferably includes a stop 8501 to assist in proper positioning of the implant body within the intervertebral space. As illustrated in FIG. 19, stop 8501 includes a stop body 8509 that provides mechanical interference with the cortical ring of the vertebral body to prevent the inserter tool 8001 from improperly positioning the implant. As illustrated, stop body 8509 has a shoulder 8507 which abuts the cortical ring of the vertebral body during insertion and thereby prevents the inserter tool 8001 and implant 1001 from being positioned too deep within the intervertebral space.

Figure 16:
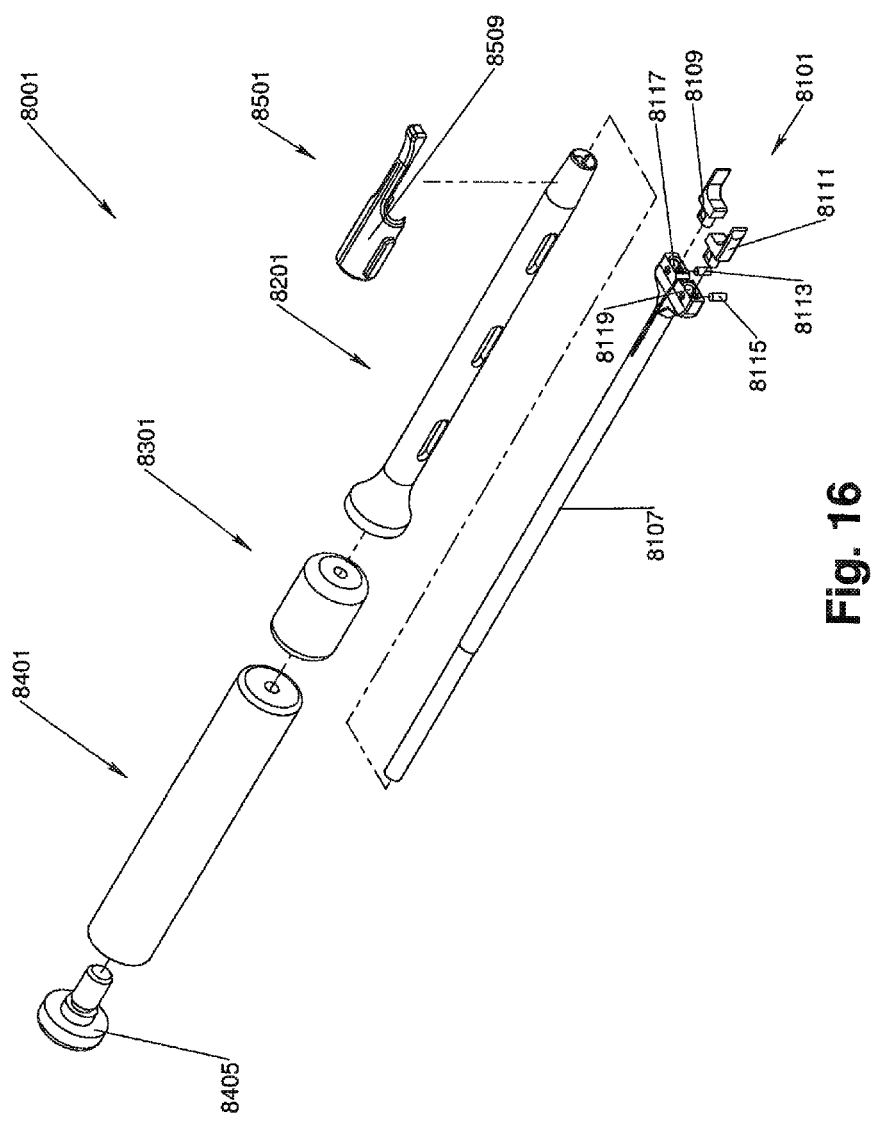
FIG. 16 is an exploded view of the implant insertion tool of FIG. 15.

As shown in FIG. 16, the stop body 8509 has a substantially cylindrical shape that conforms to the outer shaft 8201 and attaches thereto via a snap fit. Stop body 8509 includes a slit 8503 that creates resiliency in the stop body 8509 and assists in attaching and detaching the stop 8501 from the rest of the inserter tool 8001. The stop 8501 has a protuberance 8505 on each side of the stop body 8509 sized and configured to be received within one of the apertures 8203 on each side of the outer shaft 8201. Each protuberance 8505 snap fits within the aperture 8203 to further secure the stop 8501 into position on the inserter tool 8001. Because the outer shaft 8201 has numerous apertures 8203 spaced at different locations along the outer shaft 8201, the stop 8501 can be positioned at various points on the outer shaft 8201 and is thereby advantageously configured to provide mechanical interference at different depths within the intervertebral space to conform to the particular anatomy of the patient.

The method for inserting implant devices in accordance with the present invention differ from conventional insertion methods to accommodate the unique characteristics of the implant device. In particular, methods in accordance with the present invention reduce impact loading on the implants by the implant tools and by the surgical procedure used.

Preferably, the surgical procedure begins with sterilizing the surgical field and anesthetizing the patient. A surgical incision is made in the patient (preferably from the anterior, or the front of the patient). An anterior approach is generally preferable because it provides greater blood flow to promote healing and causes less tissue damage than a posterior approach (i.e. from the back of the patient). Alternatively, a lateral approach from the side of the patient can be used based on the surgeon's preference. Once the incision is made the surrounding tissue is distracted or moved out of the way using standard instruments and methodology.

In one method, the installation site of the implant is prepared by removing the severely damage tissue of the intervertebral disc (i.e. performing a discectomy). The disc may be removed with a ring curette which cuts out the disc. The endplates of the vertebra may then be roughened with the use of a rasp to remove all disc material and to encourage blood flow and healing in the vertebral space. The roughening of the endplates also flattens the surface of the vertebrae to conform to the surface of the implant and provides a textured surface to mate with the top and bottom surfaces of the implant, thus reducing the risk that the implant will shift out of position.

In a preferred method, various-sized spacer tools 4001 are then inserted into the vertebral space until the correct implant size is determined. The size is determined by first trying smaller sized trial spacer tools 4001 and progressively increasing the size of the trial spacer tool 4001 until the spacer fits into the vertebral space. Color coding or another identification system may be used to easily identify the size of implant corresponding to a given spacer.

Preferably, the next step is filling the throughbore 1009 of the implant body 1001 with bone void fillers. The synthetic bone compositions, such as synthetic bone compositions in the form of nanocrystalline HA and/or TCP that preferably make up the implant, facilitate fusion by having the characteristic of being "bioactive" which indicates the ability to facilitate a cellular or tissue response, such as, induction of vasculogenesis, promotion of cellular attachment to a scaffold material, and promotion of tissue regeneration. However, it is common practice for surgeons to further facilitate fusion of the implant by filling implants with allograft or autograft material, such as demineralized bone matrix (hereinafter DBM), as a bone void filler into and around the implantation site. The actual materials used in demineralized bone matrix (hereinafter DBM) is based on the surgeon's preference, but is typically a paste formed from the patient's blood and demineralized bone powder. DBM itself is a soft powder and has no structural properties.

The DBM crystalline structure is osteoconductive and allows bone to grow between and with the DBM crystal. DBM is also mildly osteoinductive and encourages the growth of bone cells.

Implant devices of the present invention may be filled with a paste formed from DBM and the patient's blood. Additionally, biologic materials, such as bone morphogenetic proteins (BMP) and/or bone growth stimulating compositions, are often introduced to this admixture to induce bone growth and promote fusion.

The bone growth stimulating composition preferably comprises one or more substances consisting of bone matrix, bone void filler, bone graft extender, biopolymers that stimulate bone growth, bone growth stimulating orthobiologic products, bioactive hydrogel matrix comprising a polypeptide and a long chain carbohydrate, and osteoinductive or osteoconductive materials, medicaments, stem or progenitor cells, three-dimensional structural frameworks, and the like. In some embodiments, the bone growth stimulating composition may be made from DBM.

In one preferred form, the bone growth stimulating composition comprises a cement, such as described in U.S. Patent Application Publication No. 2007/0032568, which is hereby incorporated herein in its entirety.

The preferred cement composition may include a first component and a second component. The first component preferably comprises a polymerizable resin that includes an ethylenic unsaturated double bond. The second component preferably includes a compound that includes more than one type of amine selected from the group consisting of a primary amine, a secondary amine, a tertiary amine, or a quaternary amine. The preferred cement product can also, optionally, include additional fillers, such as an inert filler or a bioactive component, that promote bone growth. In another form, the preferred cement product further comprises a third component including an oxygen-containing ring structure that is capable of reacting in a polymerization reaction with the first component, the second component or both. In yet another form, the first component further comprises an oxygen-containing ring structure that is capable of reacting in a polymerization reaction with the first component, second component, or both. In yet another form, the first component comprises at least one ethylenic unsaturated double bond and an epoxide, such as a glycidyl group. In still another form, the second component includes a polyalkyleneimine, such as polyethyleneimine (PEI) or a derivative thereof.

The bioactive component can include known bioactive materials such as densified and microporous hydroxyapatite, fluorapatite, oxyapatite, wollastonite, apatite/wollastonite glass ceramics, anorthite, calcium fluoride, calcium sulfate, agrellite, devitrite, canasite, phlogopite, monetite, brushite, octocalcium phosphate, whitlockite, cordierite, berlinite, combeite, tetracalcium phosphate, tricalcium phosphate (TCP)(e.g., .alpha.- and .beta.-tricalcium phosphates), amorphous calcium phosphate, dicalcium phosphate, phosphoric acid crystals, disodium hydrogen phosphate, and other phosphate salt-based bioceramics. Preferably the bioactive component comprises particles that are fully dense, having no internal microporosity, a particle size of about 0.5 microns to about 100 microns, and a surface area of 50 $m^2/g$ or less, 25 $m^2/g$ or less, 10 $m^2/g$ or less, 5 $m^2/g$ or less, or 2.5 $m^2/g$ or less. The particle size distribution can be broad, bimodal, or preferably trimodal, and is preferably less than about 500 micrometers, with less than 10% by weight being sub 0.5 microns sized.

In yet a further form, the filler can include biological and/or pharmaceutical agents, such as BMPs, bisphosphonates, gene delivery vectors (promoting osteogenesis or preventing osteolysis), stem cells (engineered by gene delivery vectors to upregulate expression of desired proteins such as BMPs), antiobiotics, pain killers, etc., to enhance and accelerate bone formation. The biological additive can include any suitable biological additive, including, for example plasmid DNA or RNA or proteins (e.g., bone morphogenetic proteins 2, 4, 7). The pharmaceutical additive can include any suitable pharmaceutical additive, including, for example, bisphosphonates (e.g., alendronate) and cis-platinum, antibiotics, anti-inflammatories, anti-arthritism, erythropoeitin, and the like.

The amount of filler added can represent from about 10% to about 95% by weight of the total cement mix. For example, preferably an inert filler represents from about 65% to about 85% by weight of total cement mix. Preferred densified microcrystalline and nanocrystalline bioactive hydroxyapatite, tricalcium phosphate, and bioceramic content can range from about 10% to about 99% by weight, preferably less than 85% by weight, or more preferably from about 50% to about 80% by weight of that filler.

Preferably, the bone growth stimulating composition is packed or injected into the throughbore 1009 and/or other recesses of the implant body 1001. In another form, a bioresorbable sponge is preferably fixated to the implant body to secure the bone growth stimulating composition.

The bone void filler is preferably made of synthetic materials and autograph materials (i.e., tissue that is transplanted from one portion of the patient's body to another) to eliminate the risk of infection from bone donors and reduce the risk of rejection of the bone filler by the patient's immune system. The throughbore 1009 formed by the posterior wall portion 1003 and anterior wall portion 1005 may be advantageously filled by the surgeon with such synthetic and/or autograft materials. In the instant invention, bio-compatible autograft materials from the patient's own body with synthetic extenders of the autograft material may be placed in the throughbore 1009 to encourage bone growth within and around the implant 1001.

The synthetic extenders preferably include a combination of a powder form of a calcium phosphate material such as the nanocrystalline HA and TCP materials described above, a biopolymer material that promotes bone growth and facilitates fusion, and/or autograft materials such as the patient's own blood or bone marrow. In one preferred form, the biopolymer material comprises a bioactive hydrogel matrix material utilizing E-MATRIX™ technology, such as described, for example, in U.S. Pat. Nos. 6,231,881, 6,730, 315, 6,315,994, 6,713,079, 6,261,587, 5,824,331, 6,068,974, 6,352,707, 6,270,977, 5,614,205, 6,790,455, 5,922,339, and U.S. Patent Application Publication No. 2005/0118230, all of which are hereby incorporated herein in their entireties.

Often, these biopolymers are fixated to the desired location for bone growth stimulation through use of a bioresorbable sponge. In an alternative embodiment, the bioactive hydrogel matrix material can be integrated with HA or other bone substitutes to provide sustained delivery of the bone growth stimulating compositions.

The implant body 1001 is inserted with an inserter tool such as inserter tool 6001 or inserter tool 8001. The implant body placed within the tong arms of the inserter tool, and the knob is rotated clockwise until the implant body is held securely between the tong arms. The distal end of the inserter tool, with implant attached, is then placed within the vertebral space until proper placement of the implant is achieved. The knob is then rotated counter-clockwise until the implant is released from the inserter tool. The inserter tool is then removed from the vertebral space.

Once the implant is inserted, a tamp device, such as tamp device 5001, may be required to adjust the position of the implant. The tamp device will generally be inserted and force will be directly applied by the surgeon. Alternatively, a slap-hammer can be attached to the tamp device 5001 to further position the implant.

A spinal plate may be fixed to the vertebrae to provide supplemental fixation. The supplemental fixation serves the dual purposes of providing additional structural support to the vertebrae and to provide an obstruction to the implant should the implant be expelled from the vertebral space. However, the implant body 1001 is advantageously configured to be implanted alone without the need of supplemental fixation.

The above description is not intended to be limiting on the invention, but is merely illustrative of preferred embodiments of this invention. Additional objects, features and advantages of the present invention will be apparent to those of ordinary skill in the art by referring to the above description in connection with the accompanying drawings.

What is claimed is:

1. An implant device for implantation within an intervertebral space between adjacent vertebrae, the implant device comprising:
    an implant body extending along a posterior-to-anterior axis from a posterior wall portion thereof to an anterior wall portion thereof and comprising a material selected from the group consisting of densified nanocrystalline hydroxyapatite, densified nanocrystalline tricalcium phosphate, and combinations thereof;
    an annular wall of the implant body having an inner annular surface extending about an inner void, an outer annular surface, and upper and lower vertebral engaging portions, with both the inner annular surface and the outer annular surface extending continuously without interruption between the upper and lower vertebral engaging portions so that the inner and outer annular surfaces lack any openings, channels or sharp corners;
    asymmetrical gripping structures of the upper and lower vertebral engaging portions comprising a plurality of alternating peaks and troughs, with each of the peaks having a convexly curved summit without sharp edges and each of the troughs having a concavely curved base;
    a leading portion and a trailing portion of each of the gripping structures with the leading portion and the trailing portion being differently configured relative to each other to form the asymmetrical gripping structures, wherein the leading portion, the trailing portion, the peak, and the trough for each of the gripping structures are configured in a non-overlapping orientation relative to the posterior-to-anterior axis.

2. The implant device of claim 1 wherein the leading portion of each of the gripping structures includes a flat surface extending between the convexly curved summit and the concavely curved base.

3. The implant device of claim 2, wherein the flat surface is tangent to both the convexly curved summit and the concavely curved base.

4. The implant device of claim 1 wherein the trailing portion of each of the gripping structures includes a bi-directionally continuously curved surface extending between and including the convexly curved summit and concavely curved base and configured so that the continuously curved surface is inclined from the summit to the base relative to the posterior-to-anterior axis.

5. The implant device of claim 4, wherein the convexly curved summit and the concavely curved base of the bi-directionally curved surface of the gripping structures have a junction therebetween at which the convexly curved summit and the concavely curved base are tangent to one another.

6. The implant device of claim 1 wherein the leading portion of each of the gripping structures includes a flat surface extending between the convexly curved summit and the concavely curved base, and the trailing portion of each of the gripping structures includes a bi-directionally continuously curved surface extending between and including the convexly curved summit and concavely curved base and configured so that the continuously curved surface is inclined from the summit to the base relative to the posterior-to-anterior axis.

7. The implant device of claim 1, wherein the implant body comprises densified nanocrystalline hydroxyapatite.

8. The implant device of claim 1, wherein the implant body comprises densified nanocrystalline tricalcium phosphate.

9. The implant device of claim 1, wherein the implant body comprises a combination of densified nanocrystalline hydroxyapatite, densified nanocrystalline tricalcium phosphate.

10. An implant device for implantation within an intervertebral space between adjacent vertebrae, the implant device comprising:
    an implant body extending along a posterior-to-anterior axis from a posterior wall portion thereof to an anterior wall portion thereof and comprising a material selected from the group consisting of densified nanocrystalline hydroxyapatite, densified nanocrystalline tricalcium phosphate, and combinations thereof;
    an annular wall of the implant body having an inner annular surface extending about an inner void, an outer annular surface, and upper and lower vertebral engaging portions, with both the inner annular surface and the outer annular surface extending continuously without interruption between the upper and lower vertebral engaging portions so that the inner and outer annular surfaces lack any openings, channels or sharp corners;
    asymmetrical gripping structures of the upper and lower vertebral engaging portions comprising a plurality of alternating peaks and troughs, with each of the peaks having a convexly curved summit without sharp edges and each of the troughs having a concavely curved base, each of the convexly curved summits and the concavely curved bases having radii that are centered on a line of lordosis;
    a leading portion and a trailing portion of each of the gripping structures with the leading portion and the trailing portion being differently configured relative to each other to form the asymmetrical gripping structures, wherein a flat surface is tangent to both the convexly curved summit and the concavely curved base.

11. The implant device of claim 10 wherein the leading portion, the trailing portion, the peak, and the trough for each of the gripping structures are configured in a non-overlapping orientation relative to the posterior-to-anterior axis.

* * * * *